United States Patent
Lanahan et al.

(10) Patent No.: US 6,531,648 B1
(45) Date of Patent: Mar. 11, 2003

(54) GRAIN PROCESSING METHOD AND TRANSGENIC PLANTS USEFUL THEREIN

(75) Inventors: Michael B. Lanahan, Morrisville, NC (US); Nalini Manoj Desai, Chapel Hill, NC (US); Pamela Y. Gasdaska, Carrboro, NC (US); Stephen Arthur Goff, Encinitas, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/598,747

(22) Filed: Jun. 21, 2000

Related U.S. Application Data

(63) Continuation-in-part of application No. PCT/EP99/09986, filed on Dec. 15, 1999.
(60) Provisional application No. 60/183,051, filed on Dec. 17, 1998.

(51) Int. Cl.[7] .................. C12N 15/53; C12N 15/29; C12N 5/10; C12N 15/82; A01H 5/10; A01H 5/00
(52) U.S. Cl. .................. 800/278; 800/287; 800/312; 800/320.1; 536/23.6; 435/69.1; 435/189; 435/320.1; 435/412; 435/415; 435/419
(58) Field of Search .................. 536/23.6; 435/69.1, 435/320.1, 419, 412, 415, 189; 800/278, 287, 312, 320.1

(56) References Cited

FOREIGN PATENT DOCUMENTS

| WO | WO 93 08274 | 4/1993 |
|---|---|---|
| WO | WO 96 12799 | 5/1996 |
| WO | WO 99 20122 | 4/1999 |
| WO | WO 00 14239 | 3/2000 |
| WO | WO 00 36126 | 6/2000 |
| WO | WO 00 58352 | 10/2000 |
| WO | WO 00 58453 | 10/2000 |

OTHER PUBLICATIONS

Jacquot et al. J. Mol. Biol. 235(4): 1357–1363, 1994.*
Buchanan et al., *Thioredoxin: A multifunctional regulatory protein with a Bright Future in Technology and Medicine Archives of Biochemistry and Biophysics*, vol. 314, No. 2 (Nov. 1, 1994) pp. 257–260.
Cho et al., *Overexpression of Thioredoxin H Leads to Enhanced Activity of Starch Debranching Enzyme (Pullulanase) in Barley Grain Proceedings of the National Academy of Sciences of USA*, vol. 96, No. 25 (Dec. 1999) pp. 14641–14646.
Jacquot et al, *A. thaliana mRNA for NADPH thioredoxin reductase* Accession No.: Z23109 [database, EMBL online], URL: http:www.ebi.ac.uk/cgi–bin/emblfetch.
Singh et al, *Wet Milling of Corn –Review of Laboratory– Scale and Pilot Plant–Scale Procedures Cereal Chemistry*, vol. 73, No. 6 (Nov. 1, 1996), pp. 659–667.

* cited by examiner

Primary Examiner—David T. Fox
(74) Attorney, Agent, or Firm—Marcia R. Morton

(57) ABSTRACT

The invention provides novel methods of processing grain, such as corn and soybeans, utilizing thioredoxin and/or thioredoxin reductase to enhance extractability and recovery of starch and protein. The invention further provides novel transgenic plants expressing thermostable thioredoxin and/or thioredoxin reductase.

8 Claims, No Drawings

US 6,531,648 B1

GRAIN PROCESSING METHOD AND TRANSGENIC PLANTS USEFUL THEREIN

This application is a continuation-in-part of Application No. PCT/EP99/09986, filed Dec. 15, 1999, which claims benefit of U.S. patent application No. 09/213,208, filed Dec. 17, 1998, converted to provisonal application 60/183,051, filed Dec. 17, 1998.

FIELD OF THE INVENTION

This invention relates to improved methods of grain processing to enhance protein and starch recovery, particularly in corn wet milling and soybean processing, as well as novel transgenic plants useful in such processes.

BACKGROUND OF THE INVENTION

Thioredoxin (TRX) and thioredoxin reductase (TR) are enzymes that use NADPH to reduce disulphide bonds in proteins. Protein disulphide bonds play an important role in grain processing efficiencies and in the quality of the products recovered from grain processing. Development of effective ways to eliminate or decrease the extent of protein disulphide bonding in grain would increase processing efficiencies. Additionally, grain and grain-derived product performance in livestock feed are also affected by inter- and intramolecular disulphide bonding. Grain digestibility, nutrient availability and the neutralization of anti-nutritive factors (e.g., protease, amylase inhibitors etc.) would be increased by reducing the extent of disulphide bonding. See, PCT/EP99/09986, filed Dec. 15, 1999, and U.S. Provisional Application No. 60/183,051, filed Dec. 17, 1998, both of which are incorporated herein by reference.

SUMMARY OF THE INVENTION

Expression of transgenic thioredoxin and/or thioredoxin reductase in corn and soybeans and the use of thioredoxin in grain processing, e.g., wet milling, is novel and provides an alternative method for reducing the disulfide bonds in seed proteins during or prior to industrial processing. The invention therefore provides grains with altered storage protein quality as well as grains that perform qualitatively differently from normal grain during industrial processing or animal digestion (both referred to subsequently as "processing").

This method of delivery of thioredoxin and/or thioredoxin reductase eliminates the need to develop exogenous sources of thioredoxin and/or thioredoxin reductase for addition during processing. A second advantage to supplying thioredoxin and/or thioredoxin reductase via the grains is that physical disruption of seed integrity is not necessary to bring the enzyme in contact with the storage or matrix proteins of the seed prior to processing or as an extra processing step.

Three modes of thioredoxin utilization in grain processing are provided:

1. Expression and action during seed development to alter the composition and quality of harvested grain;
2. Expression (but no activity) during seed development to alter the quality of the products upon processing;
3. Production of thioredoxin and/or thioredoxin reductase in grain that is used to alter the quality of other grain products by addition during processing.

The invention described herein is applicable to all grain crops, in particular corn, soybean, wheat, and barley, most particularly corn and soybean, especially corn. Expression of transgenic thioredoxin and/or thioredoxin reductase in grain is a means of altering the quality of the material (seeds) going into grain processing, altering the quality of the material derived from grain processing, maximizing yields of specific seed components during processing (increasing efficiency), changing processing methods, and creating new uses for seed-derived fractions or components from milling streams.

The invention thus provides a plant which expresses a thioredoxin and/or thioredoxin reductase, e.g. a thioredoxin and/or thioredoxin reductase not naturally expressed in plants, for example a plant comprising a heterologous DNA sequence coding for a thioredoxin stably integrated into its nuclear or plastid DNA, preferably under control of an inducible promoter, e.g., a chemically-inducible promoter, for example either operatively linked to the inducible promoter or under control of transactivator-regulated promoter wherein the corresponding transactivator is under control of the inducible promoter or is expressed in a second plant such that the promoter is activated by hybridization with the second plant; wherein the thioredoxin or thioredoxin reductase is preferably thermostable; such plant also including seed therefor, which seed is optionally treated (e.g., primed or coated) and/or packaged, e.g. placed in a bag with instructions for use, and seed harvested therefrom, e.g., for use in a milling process as described above.

The transgenic plant of the invention may optionally further comprise genes for enhanced production of thioredoxin reductase and/or NADPH.

The invention further provides a method for producing a thioredoxin comprising cultivating a thioredoxin-expressing plant as described above; a method for producing starch and/or protein comprising extracting starch or protein from seed harvested from a plant as described above; and a method for wet milling comprising steeping seed from a thioredoxin-expressing plant as described above and extracting starch and/or protein therefrom.

The invention further provides a plant expressible expression cassette comprising a coding region for a thioredoxin or thioredoxin reductase, preferably a thioredoxin derived from a thermophilic organism, e.g., from an archea, for example from *Methanococcus jannaschii* or *Archaeglobus fulgidus*, e.g., as described below, wherein the coding region is preferably optimized to contain plant preferred codons, said coding region being operatively linked to promoter and terminator sequences which function in a plant, wherein the promotor is preferably a seed specific promoter or an inducible promoter, e.g., a chemically inducible or transactivator-regulated promoter; for example a plastid or nuclear expressible expression cassette comprising a promoter, e.g., a transactivator-mediated promoter regulated by a nuclear transactivator (e.g., the T7 promoter when the transactivator is T7 RNA polymerase the expression of which is optionally under control of an inducible promoter).

The invention further provides a vector comprising such a plant expressible expression cassette.

The invention further provides a plant transformed with such a vector, or a transgenic plant which comprises in its genome, e.g., its nuclear or plastid genome, such a plant expressible expression cassette.

The invention also comprises a method of producing grain comprising high levels of thioredoxin or thioredoxin reductase comprising pollinating a first plant comprising a heterologous expression cassette comprising a transactivator-mediated promoter regulated and operatively linked to a DNA sequence coding for a thioredoxin or thioredoxin reductase, the first plant preferably being emasculated or male sterile, with pollen from a second plant comprising a heterologous expression cassette comprising a promoter operatively linked to a DNA sequence coding for a transactivator capable of regulating said transactivator-mediated promoter, and recovering grain from the plant thus pollinated.

The invention also provides a nucleic acid molecule comprising a nucleotide sequence encoding an Arabidopsis NADPH$^+$ dependent thioredoxin reductase (NTR), wherein the nucleotide sequence is optimized for expression in a monocotyledonous plant, preferably optimized for expression in maize. The nucleotide sequence is preferably the nucleotide sequence of SEQ ID NO:24 and preferably encodes the amino acid sequence of SEQ ID NO:25.

The invention also provides an isolated nucleic molecule comprising a nucleotide sequence encoding a rice NADPH$^+$ dependent thioredoxin reductase (NTR). The nucleotide sequence preferably encodes the amino acid sequence of SEQ ID NO:27. The nucleotide sequence is preferably the nucleotide sequence of SEQ ID NO:25.

BRIEF DESCRIPTION OF THE SEQUENCE LISTING

SEQ ID NO:1—Protein sequence of thioredoxin from *Methanococcus jannaschii* (gi|1591029).
SEQ ID NO:2—Protein sequence of thioredoxin from *Archaeoglobus fulgidus* (gi|2649903)(trx-1).
SEQ ID NO:3—Protein sequence of thioredoxin from *Archaeoglobus fulgidus* (gi|2649838) (trx-2).
SEQ ID NO:4—Protein sequence of thioredoxin from *Archaeoglobus fulgidus* (gi|2649295) (trx-3).
SEQ ID NO:5—Protein sequence of thioredoxin from *Archaeoglobus fulgidus* (gi|2648389) (trx-4).
SEQ ID NO:6—Protein sequence of thioredoxin reductase (trxB) from *Methanococcus jannaschii* (gi|592167).
SEQ ID NO:7—Protein sequence of thioredoxin reductase from *Archaeoglobus fulgidus* (gi|2649006) (trxB).
SEQ ID NO:8—Primer NMD109.
SEQ ID NO:9—Primer NMD110.
SEQ ID NO:10—Primer NMD102.
SEQ ID NO:11—Primer NMD103.
SEQ ID NO:12—Primer NMD124A.
SEQ ID NO:13—Primer NMD125A.
SEQ ID NO:14—Primer NMD126.
SEQ ID NO:15—Primer NMD127.
SEQ ID NO:16—Primer NMD128.
SEQ ID NO:17—Primer NMD129.
SEQ ID NO:18—Primer STRF1A.
SEQ ID NO:19—Primer STRF1B.
SEQ ID NO:20—Primer STRF2A.
SEQ ID NO:21—Primer STRF2B.
SEQ ID NO:22—Primer STR3A.
SEQ ID NO:23—Primer STR3B.
SEQ ID NO:24—Maize optimized Arabidopsis NADPH dependent thioredoxin reductase coding sequence.
SEQ ID NO:25—Amino acid sequence encoded by SEQ ID NO:24.
SEQ ID NO:26—Rice NADPH dependent thioredoxin reductase (NTR) coding sequence.
SEQ ID NO:27—Amino acid sequence encoded by SEQ ID NO:26.
SEQ ID NO:28—Primer P9.
SEQ ID NO:29—Primer P10.
SEQ ID NO:30—Primer P4.
SEQ ID NO:31—Primer P1.
SEQ ID NO:32—Primer P2.
SEQ ID NO:33—Primer P5.
SEQ ID NO:34—Primer P12.
SEQ ID NO:35—Primer P11.
SEQ ID NO:36—Primer P27.
SEQ ID NO:37—Primer P28.
SEQ I) NO:38—Primer P29.
SEQ ID NO:39—Primer P26.
SEQ ID NO:40—Primer P31.
SEQ ID NO:41—Primer Thiorodoxubi 1603.
SEQ ID NO:42—Primer Thiorodox 2364.

DEFINITIONS

"Associated with/operatively linked" refer to two nucleic acid sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

A "chimeric gene" is a recombinant nucleic acid sequence in which a promoter or regulatory nucleic acid sequence is operatively linked to, or associated with, a nucleic acid sequence that codes for an mRNA or which is expressed as a protein, such that the regulator nucleic acid sequence is able to regulate transcription or expression of the associated nucleic acid sequence. The regulator nucleic acid sequence of the chimeric gene is not normally operatively linked to the associated nucleic acid sequence as found in nature.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

Complementary: "complementary" refers to two nucleotide sequences that comprise antiparallel nucleotide sequences capable of pairing with one another upon formation of hydrogen bonds between the complementary base residues in the antiparallel nucleotide sequences.

DNA Shuffling: DNA shuffling is a method to rapidly, easily and efficiently introduce mutations or rearrangements, preferably randomly, in a DNA molecule or to generate exchanges of DNA sequences between two or more DNA molecules, preferably randomly. The DNA molecule resulting from DNA shuffling is a shuffled DNA molecule that is a non-naturally occurring DNA molecule derived from at least one template DNA molecule. The shuffled DNA encodes an enzyme modified with respect to the enzyme encoded by the template DNA, and preferably has an altered biological activity with respect to the enzyme encoded by the template DNA.

Enzyme/Protein Activity: means herein the ability of an enzyme (or protein) to catalyze the conversion of a substrate into a product. A substrate for the enzyme comprises the natural substrate of the enzyme but also comprises analogues of the natural substrate, which can also be converted, by the enzyme into a product or into an analogue of a product. The activity of the enzyme is measured for example by determining the amount of product in the reaction after a certain period of time, or by determining the amount of substrate remaining in the reaction mixture after a certain period of time. The activity of the enzyme is also measured by determining the amount of an unused co-factor of the reaction remaining in the reaction mixture after a certain period of time or by determining the amount of used co-factor in the reaction mixture after a certain period of time. The activity of the enzyme is also measured by determining the amount of a donor of free energy or energy-rich molecule (e.g. ATP, phosphoenolpyruvate, acetyl phosphate or phosphocreatine) remaining in the reaction mixture after a certain period of time or by determining the amount of a used donor of free energy or energy-rich molecule (e.g. ADP, pyruvate, acetate or creatine) in the reaction mixture after a certain period of time.

Expression Cassette: "Expression cassette" as used herein means a DNA sequence capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter which initiates transcription only when the host cell is exposed to some particular external stimulus. In the case of a multicellular organism, such as an insect, the promoter can also be specific to a particular tissue or organ or stage of development.

Gene: the term "gene" is used broadly to refer to any segment of DNA associated with a biological function. Thus, genes include coding sequences and/or the regulatory sequences required for their expression. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

Heterologous DNA Sequence: The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also includes non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

Homologous DNA Sequence: a DNA sequence naturally associated with a host cell.

"Homoplastidic" refers to a plant, plant tissue or plant cell wherein all of the plastids are genetically identical. This is the normal state in a plant when the plastids have not been transformed, mutated, or otherwise genetically altered. In different tissues or stages of development, the plastids may take different forms, e.g., chloroplasts, proplastids, etioplasts, amyloplasts, chromoplasts, and so forth.

Isolated: in the context of the present invention, an isolated DNA molecule or an isolated enzyme is a DNA molecule or protein which, by the hand of man, exists apart from its native environment and is therefore not a product of nature. An isolated DNA molecule or protein may exist in a purified form or may exist in a non-native environment such as, for example, in a transgenic host cell.

Mature Protein: protein that is normally targeted to a cellular organelle and from which the transit peptide has been removed.

Minimal Promoter: promoter elements, particularly a TATA element, that are inactive or that have greatly reduced promoter activity in the absence of upstream activation. In the presence of a suitable transcription factor, the minimal promoter functions to permit transcription.

Modified Enzyme Activity: enzyme activity different from that which naturally occurs in an insect (i.e. enzyme activity that occurs naturally in the absence of direct or indirect manipulation of such activity by man), which is tolerant to inhibitors that inhibit the naturally occurring enzyme activity.

Native: refers to a gene that is present in the genome of an untransformed insect cell.

Naturally occurring: the term "naturally occurring" is used to describe an object that can be found in nature as distinct from being artificially produced by man. For example, a protein or nucleotide sequence present in an organism (including a virus), which can be isolated from a source in nature and which has not been intentionally modified by man in the laboratory, is naturally occurring.

Nucleic acid: the term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19: 5081 (1991); Ohtsuka et al., *J. Biol. Chem.* 260: 2605–2608 (1985); Rossolini et al., *Mol. Cell. Probes* 8: 91–98 (1994)). The terms "nucleic acid" or "nucleic acid sequence" may also be used interchangeably with gene, cDNA, and mRNA encoded by a gene.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "promoter" is an untranslated DNA sequence upstream of the coding region that contains the binding site for RNA polymerase II and initiates transcription of the DNA. The promoter region may also include other elements that act as regulators of gene expression.

A "protoplast" is an isolated plant cell without a cell wall or with only parts of the cell wall.

Purified: the term "purified," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. The term "purified" denotes that a nucleic acid or protein gives rise to essentially one band in an electrophoretic gel. Particularly, it means that the nucleic acid or protein is at least about 50% pure, more preferably at least about 85% pure, and most preferably at least about 99% pure.

"Regulatory elements" refer to sequences involved in controlling the expression of a nucleotide sequence. Regulatory elements comprise a promoter operatively linked to the nucleotide sequence of interest and termination signals. They also typically encompass sequences required for proper translation of the nucleotide sequence.

Significant Increase: an increase in enzymatic activity that is larger than the margin of error inherent in the measurement technique, preferably an increase by about 2-fold or greater of the activity of the wild-type enzyme in the presence of the inhibitor, more preferably an increase by about 5-fold or greater, and most preferably an increase by about 10-fold or greater.

The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

Substantially identical: the phrase "substantially identical," in the context of two nucleic acid or protein sequences, refers to two or more sequences or subsequences that have at least 60%, preferably 80%, more preferably 90–95%, and most preferably at least 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions. Furthermore, substantially identical nucleic acid or protein sequences perform substantially the same function.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci.* USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), of by visual inspection (see generally, Ausubel et al., infra).

One example of an algorithm that is suitable for determining percent sequence identity and sequence similarity is the BLAST algorithm, which is described in Altschul :et al., *J. Mol. Biol.* 215: 403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci.* USA 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci.* USA 90: 5873–5787

(1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another indication that two nucleic acid sequences are substantially identical is that the two molecules hybridize to each other under stringent conditions. The phrase: "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) *Laboratory Techniques in Biochemistry and Molecular Biology-Hybridization with Nucleic Acid Probes* part I chapter 2 "Overview of principles of hybridization and the strategy of nucleic acid probe assays" Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS); 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO4, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.

A further indication that two nucleic acid sequences or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

The phrase "specifically (or selectively) binds to an antibody," or "specifically (or selectively) immunoreactive with," when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised to the protein with the amino acid sequence encoded by any of the nucleic acid sequences of the invention can be selected to obtain antibodies specifically immunoreactive with that protein and not with other proteins except for polymorphic variants. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See Harlow and Lane (1988) *Antibodies, A Laboratory Manual*, Cold Spring Harbor Publications, New York "Harlow and Lane"), for a description of immunoassay formats and conditions that can be used to determine specific immunoreactivity. Typically a specific or selective reaction will be at least twice background signal or noise and more typically more than 10 to 100 times background.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a protein also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a protein is implicit in each described sequence.

Furthermore, one of skill will recognize that individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid: (E), Asparagine (N), Glutamine (Q). See also, Creighton (1984) Proteins, W. H. Freeman and Company. In addition, individual substitutions, deletions or additions which alter, add or delete a single amino acid or a small percentage of amino acids in an encoded sequence are also "conservatively modified variations."

A "subsequence" refers to a sequence of nucleic acids or amino acids that comprise a part of a longer sequence of nucleic acids or amino acids (e.g., protein) respectively.

Nucleic acids are "elongated" when additional nucleotides (or other analogous molecules) are incorporated into the nucleic acid. Most commonly, this is performed with a polymerase (e.g., a DNA polymerase), e.g., a polymerase which adds sequences at the 3' terminus of the nucleic acid.

Two nucleic acids are "recombined" when sequences from each of the two nucleic acids are combined in a progeny nucleic acid. Two sequences are "directly" recombined when both of the nucleic acids are substrates for recombination. Two sequences are "indirectly recombined" when the sequences are recombined using an intermediate such as a cross-over oligonucleotide. For indirect recombination, no more than one of the sequences is an actual substrate for recombination, and in some cases, neither sequence is a substrate for recombination.

"Synthetic" refers to a nucleotide sequence comprising structural characters that are not present in the natural sequence. For example, an artificial sequence that resembles more closely the G+C content and the normal codon distribution of dicot and/or monocot genes is said to be synthetic.

A "transactivator" is a protein which, by itself or in combination with one or more additional proteins, is capable of causing transcription of a coding region under control of a corresponding transactivator-mediated promoter. Examples of transactivator systems include phage T7 gene 10 promoter, the transcriptional activation of which is dependent upon a specific RNA polymerase such as the phage T7 RNA polymerase. The transactivator is typically an RNA polymerase or DNA binding protein capable of interacting with a particular promoter to initiate transcription, either by activating the promoter directly or by inactivating a repressor gene, e.g., by suppressing expression or accumulation of a repressor protein. The DNA binding protein may be a chimeric protein comprising a binding region (e.g., the GAL4 binding region) linked to an appropriate transcriptional activator domain. Some transactivator systems may have multiple transactivators, for example promoters which require not only a polymerase but also a specific subunit (sigma factor) for promotor recognition, DNA binding, or transcriptional activation. The transactivator is preferably heterologous with respect to the plant.

Transformation: a process for introducing heterologous DNA into a cell, tissue, or insect. Transformed cells, tissues, or insects are understood to encompass not only the end product of a transformation process, but also transgenic progeny thereof.

"Transformed," "transgenic," and "recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed," "non-transgenic," or "non-recombinant" host refers to a wild-type organism, e.g., a bacterium or plant, which does not contain the heterologous nucleic acid molecule.

Nucleotides are indicated by their bases by the following standard abbreviations: adenine (A), cytosine (C), thymine (T), and guanine (G). Amino acids are likewise indicated by the following standard abbreviations: alanine (Ala; A), arginine (Arg; R), asparagine (Asn; N), aspartic acid (Asp; D), cysteine (Cys; C), glutamine (Gln; Q),glutamic acid (Glu; E), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V). Furthermore, (Xaa; X) represents any amino acid.

DETAILED DESCRIPTION OF THE INVENTION

Wet Milling

Wet milling is a process of separating the starch, protein and oil components of grain, most often cereals, for example corn. It is distinguished herein from dry milling, which is simply pulverizing grain. Corn wet milling is comprised of the steps of steeping, grinding the corn kernel and separating the components of the kernel. The first step in wet milling is usually steeping, wherein the grain is soaked in water under carefully controlled conditions to soften the kernels and facilitate separation of the components. The kernels are typically steeped in a steep tank with a countercurrent flow of water at about 120° F. containing sulfur dioxide at a concentration of about 0.2% by weight. The kernels remain in the steep tank from about 24 to 48 hours. The kernels are then dewatered and subjected to sets of attrition type mills. The first set of attrition type mills rupture the kernels releasing the germ, and corn oil from the rest of the kernel.

Centrifugation is used to separate the germ from the rest of the kernel. The oil-bearing embryos float to the surface of the aqueous solution and are removed.

Next, by processes of watering and dewatering, milling, screening, centrifuging and washing, the starch is separated from the protein and purified. Following embryo removal, the remaining kernel components including the starch, hull, fiber, and gluten are subjected to another set of attrition mills and passed through a set of wash screens to separate the fiber components from the starch and gluten. The starch and gluten pass through the screens while the fiber does not. Centrifugation or a third grind followed by centrifugation is used to separate the starch from the protein. Centrifugation produces a slurry containing the starch granules, which is dewatered, washed with fresh water and dried to about 12% moisture. The result is the recovery of a fraction of substantially pure starch from the corn kernels in this manner.

The key difficulty is to loosen starch granules from the complicated matrix of proteins and cell wall material that makes up the endosperm of the grain. One reason for this difficulty is believed to be the presence of inter- or intramolecular disulfide bonds, which render the protein matrix less soluble and less susceptible to proteolytic enzymes and inhibit release of the starch granules from the protein matrix in the grain. At present, the primary means for reducing these bonds is to steep the grain in the presence of sulfur dioxide, but this is costly, environmentally unfriendly, and not optimally effective. Because the steep water contains sulfur dioxide it is considered toxic waste, and therefore minimizing the volume generated would be advantageous. Alternatively, the requirement for sulfur dioxide would be eliminated. Reducing the steep times that are required for grain conditioning prior to milling is an additional advantage of reducing the extent of disulfide bonds in the endosperm matrix.

Certain mutations exert beneficial effects on the protein matrix of corn kernel endosperm (floury and opaque), but impair kernel integrity. Transgenic thioredoxin expression provides some of these advantages without creating some of the kernel integrity problems associated with these mutations.

Post-harvest or processing-dependent activities of thioredoxin have equally beneficial effects. For example, in one embodiment, thioredoxin and/or thioredoxin reductase enzymes are targeted to and accumulated in cell compartments. Protein reduction occurs following physical disruption of the seed. In another embodiment, quiescent endosperm thioredoxin and/or thioredoxin reductase is activated upon steeping. In a preferred embodiment, the invention provides a plant expressing a transgenic thermostable thioredoxin and thioredoxin reductase, e.g. a thioredoxin and thioredoxin reductase derived from a hyperthermophilic organism, such that the thioredoxin and thioredoxin reductase are not significantly active except at high temperatures (e.g., greater than 50° C.). In one embodiment, the thermnostable thioredoxin and thioredoxin reductase are synergistic with saccharification via expression of other thermostable enzymes in endosperm.

Feed Applications

Expression of transgenic thioredoxin and/or thioredoxin reductase in grain is also useful to improve grain characteristics associated with digestibility, particularly in animal feeds. Susceptibility of feed proteins to proteases is a function of time and of protein conformation. Kernel cracking is often used in feed formulation as is steam flaking. Both of these processes are designed to aid kernel digestibility. Softer kernels whose integrity can be disrupted more easily in animal stomachs are desirable. Conformational constraints and crosslinks between proteins are major determinants of protease susceptibility. Modifying these bonds by increased thioredoxin and/or thioredoxin reductase expression thereby aids digestion.

Corn Dry Milling/masa

Protein content and quality are important determinants in flaking grit production and in masa production. Reduction of disulphide bonds alters the nature of corn flour such that it is suitable for use as a wheat substitute, especially flours made from high-protein white corn varieties.

Soybean Crushing

Over half of the US soybean crop is crushed or milled, and the protein quality in the resulting low-fat soy flour or de-fatted soy flour (or soybean meal) is important for subsequent processing. Protein yield and quality from soybean processing streams are economically important, and are largely dependent upon protein conformation. Increasing thioredoxin activity through expression of transgenic thioredoxin and/or thioredoxin reductase increases protein solubility, and thus increases yield, in the water-soluble protein fractions. Recovery is facilitated by aqueous extraction of de-fatted soybean meal under basic conditions. Enhancing thioredoxin activity through expression of transgenic thioredoxin and/or thioredoxin reductase also reduces the required pH for efficient extraction and thereby reduces calcium or sodium hydroxide inputs, as well as lowering the acid input for subsequent acid precipitation, allowing efficient recovery of proteins without alkali damage, and reducing water consumption and processing plant waste effluents (that contain substantial biological oxygen demand loads).

Protein redox status affects important functional properties supplied by soy proteins, such as solubility, water absorption, viscosity, cohesion/adhesion, gelation and elasticity. Fiber removal during soy protein concentrate production and soy protein isolate hydrolysis by proteases is enhanced by increasing thioredoxin activity as described herein. Similarly, as described for corn above, increasing thioredoxin activity through expression of transgenic thioredoxin and/or thioredoxin reductase enhances the functionality of enzyme-active soy flours and the digestibility of the soybean meal fraction and steam flaking fraction in animal feeds.

Modification of protein quality during seed development and during processing are both provided, although it is preferred that the transgenic thioredoxin and/or thioredoxin reductase be targeted to a cell compartment and be thermostable, as described above, to avoid significant adverse effects on storage protein accumulation possibly encountered as a result of thioredoxin activity during seed development. Alternately, the thioredoxin may be added as a processing enzyme, as (in contrast to corn wet milling) breaking the disulphide bonds is not necessary until after grain integrity is destroyed (crushing and oil extraction).

Selection of Thioredoxin and Thioredoxin Reductase for Heterologous Expression Thioredoxin, thioredoxin reductase and protein disulfide isomerase (PDI) genes are found in eukaryotes, eubacteria as well as archea, including hyperthermophilic organisms such as *Methanococcus jannaschii* and *Archaeoglobus fulgidus*. Selection of a particular gene depends in part on the desired application. For the methods of the present invention, preferred thioredoxins have the following characteristics:

1. Heat stability—Thioredoxin and related proteins from hyperthermophiles are found to have increased stability at high temperatures (>50° C.) and relatively low activity at ambient temperatures. Expression of thioredoxin and/or thioredoxin reductase from hyperthermophiles, for example from archea such as *Methanococcus jannaschii* and *Archaeoglobus fulgidus* or other hyperthermophiles is preferred for expression during seed development, so that the thioredoxin activity is not markedly increased until the grain is steeped or processed at elevated temperature. Most grain processing methods involve, or are compatible with, a high temperature step. Thermostable thioredoxin and thioredoxin reductase are therefore preferred. By thermostable is meant that the enzyme is preferentially active at high temperatures, e.g., temperatures greater than 40° C., most preferably greater than 50° C., e.g. 45–60° C. for wet milling, or even higher, e.g., 45–95° C.

2. Substrate specificity—It is also possible to reduce undesirable effects on seed development by selection of a thioredoxin that acts preferentially on certain proteins such as the structural protein in the matrix and has low activity with essential metabolic enzymes. Various thioredoxins have been shown to differ in reactivity with enzymes that are under redox control. Thus it is possible to select a thioredoxin that will primarily act on the desired targets, minimizing undesirable side-effects of over expression.

Suitable thermostable thioredoxins and thioredoxin reductases include the following:

amino acid sequence of thioredoxin from *Methanococcus jannaschii* (gi|1591029) MSKVKIELFTSPMCPHC-PAAKRVVEEVANEMPDAVEVEYINVMEN-PQKAMEYGIMA VPTIVINGDVEFIGAPT-KEALVEAIKKRL (SEQ ID NO:1);

amino acid sequence of thioredoxin from *Archaeoglobus fulgidus* (gi|2649903)(trx-1) MPMVRKAAFYAIA-VISGVLAAVVGNALYHNFNSDLGAQAK-IYFFYSDSCPHCREVKP YVEEFAKTHNLTWCN-VAEMDANCSKIAQEFGIKYVPTLVIMDEEAHVF VGSDEVRTA IEGMK (SEQ ID NO:2);

amino acid sequence of thioredoxin from *Archaeoglobus fulgidus* (gi|2649838)(trx-2) MVFTSKYCPY-CRAFEKVVERLMGELNGTVEFEVVDVDE-KRELAEKYEVLML PTLVLADGDEVLGGFMG-FADYKTAREAILEQISAFLKPDYKN (SEQ ID NO:3);

amino acid sequence of thioredoxin from *Archaeoglobus fulgidus* (gi|2649295)(trx-3) MDELE-LIRQKKLKEMMQKMSGEEKARKVLD-SPVKLNSSNFDETLKNNENVVVDFW AEWC-MPCKMIAPVEELAKEYAGKVVFGKLNTDENPT IAARYGISAIPTLIFFKKGKPV DQLVGAMPK-SELKRWVQRNL (SEQ ID NO:4);

amino acid sequence of thioredoxin from *Archaeoglobus fulgidus* (gi|2648389)(trx-4) MERLNSERFREVIQSD-KLVVVDFYADWCMPCRYISPELEKLS-KEYNGEVEFYKLNVDE NQDVAFEYGIAS IPTV-LFFRNGKVVGGFIGAMPESAVRAEIEKALGA (SEQ ID NO:5);

amino acid sequence of thioredoxin reductase (trxB) from *Methanococcus jannaschii* (gi|1592167) MIHDTIIIGAGPGGLTAGIYAMRGKL-NALCIEKENAGGRIAEAGIVENYPGFEEI RGYE-LAEKFKNHAEKFKLPIIYDEVIKIETK-ERPFKVITKNSEYLTKTIVIATGTKPKKL GLNEDKFIGRGISYCTMCDAF-FYLNKEVIVIGRDTPAIMSAINLKDI-AKKVIVITDKSEL KAAESIMLDKLKEANNVEI-IYNAKPLEIVGEERAEGVKISVNGKEEIIKADGI RSLGHV PNTEFLKDSGELDKKGFIKTDENCRT-NIDGIYAVGDVRGGVMQVAKAVGDGCVAM ANIIKYLQKL (SEQ ID NO:6); and amino acid sequence of thioredoxin reductase from *Archaeoglobus fulgidus* (gi|2649006)(trxB) MYDVAI-IGGGPAGLTAALYSARYGLKTVFFETVD-PVSQLSLAAKIENYPGFEGSGMEL LEK-MKEQAVKAGAEWKLEKVERVERNGETFTVIA EGGEYEAKAIIVATGGKHKEAGI EGESAFI-GRGVSYCATCDGNFFRGKKVIVYGS-GKEAIEDAIYLHDIGCEVTIVSRTPSFR AEKALVEEVEKRGIPVEIYSTTIRKI-IGSGKVEKVVAYNREKKEEFE IEADGIFVAIGMR PATDVVAELGVERDSMGYIKVDKEQRT-NVEGVFAAGDCCDNPLKQVVTACGDGAV AAY-SAYKYLTS (SEQ ID NO:7).

The genes that encode these proteins for use in the present invention are preferably designed by back-translation using plant preferred codons, to enhance G–C content and remove detrimental sequences, as more fully described below. The activity of the proteins may be enhanced by DNA shuffling or other means, as described below. The invention therefore comprises proteins derived from these proteins, especially proteins which are substantially similar which retain thioredoxin or thioredoxin reductase activity.

For engineering thioredoxin expression in seeds for activity during grain development, promoters which direct seed-specific expression of thioredoxin and thioredoxin reductase are preferred, as is targeting to the storage so that the enzyme will have the desired effects on storage proteins, which may be desirable in some applications. In the present invention, however, it is more generally desirable to engineer thioredoxin and/or thioredoxin reductase expression in seeds for accumulation and inactivity during grain development. Several strategies are employed to create seeds that express transgenic thioredoxin and/or thioredoxin reductase without having a significant impact on normal seed development, e.g.:

(i) To compartmentalize active thioredoxin or thioredoxin reductase such that it does not significantly interact with the target proteins, for example by targeting to or expression in amyloplasts. Plastid targeting sequences are used to direct accumulation in the amyloplast. Alternatively, the thioredoxin and/or thioredoxin reductase is targeted to an extracellular location in cell walls using secretion signals. Or finally, in the case of monocots,:expression in cell types such as aleurone during seed development is used to keep the thioredoxin and/or thioredoxin reductase away from the storage components of the rest of the endosperm.

(ii) To engineer the expression of thioredoxin and/or thioredoxin reductase from thermophilic organisms. Enzymes which have little or no activity at ambient temperatures (as high as 38–39° C. in the field) are less likely less likely to cause problems during development. Preferably, therefore, the enzymes are active primarily at high temperatures, e.g., temperatures greater than 40° C., most preferably 45–60° C. for wet milling, or even higher, e.g., 45–95° C.

(iii) To place the thioredoxin and/or thioredoxin reductase under control of an inducible promoter, for example a chemically-inducible promoter, a wound inducible promoter, or a transactivator mediated promotor which is activated upon pollination by a plant expressing the transactivator.

(iv) To utilize thioredoxin having specific requirements for a particular thioredoxin reductase, such that activity of the thioredoxin or thioredoxin reductase is suitably regulated via availability of the appropriate thioredoxin reductase or thioredoxin, respectively. For example, the thioredoxin and thioredoxin reductase are expressed in different plants, so that the active combination is only available in the seed upon pollination by the plant expressing the complimentary enzyme. Alternatively, the thioredoxin or thioredoxin reductase is sequestered in the cell, for example in a plastid, vacuole, or apoplast, as described above, so that it does not become available until the grain is processed.

Methods of Grain Processing

The invention thus provides a novel method of enhancing separation of the starch from the protein matrix, using thioredoxin and/or thioredoxin reductase. In a first embodiment, thioredoxin activity is found to be useful in a variety of seed processing applications, including wet milling, dry milling, oilseed processing, soybean processing, wheat processing and flour/dough quality, most especially the wet milling of grains, in particular corn.

Accordingly, the invention provides a method to improve milling efficiency or increase milling yield, to increase efficiency of separation of starch and protein, to enhance yields of starch and soluble proteins from grain, or to enhance increase protein solubility in water or other solvents, comprising steeping grain in the presence of supplemental thioredoxin and/or thioredoxin and separating the starch and protein components of the grain. Typically, steeping occurs before milling, but may occur afterwards, and there may be more than one milling or steeping step in the process method extraction and increase protein yield from seeds during the steep or points after steeping. Preferably, the supplemental thioredoxin and/or thioredoxin reductase is provided by expression of a transgene in the plant from which the grain is harvested.

The invention further provides: the use of thioredoxin or thioredoxin reductase in a method to improve milling efficiency or increase milling yield of starches or proteins, for example in any of the methods described above, steepwater comprising an amount of thioredoxin and/or thioredoxin reductase effective to facilitate separation of starch from protein in grain; grain which has been exposed to thioredoxin an amount effective to facilitate separation of starch from protein; and starch or protein which has been produced by the method described above.

The activity of the thioredoxin in the above method may be enhanced by supplementing the steepwater with thioredoxin reductase and/or NADPH. Other components normally present in steepwater for wet milling may also be present, such as bacteria which produce lactic acid. Preferably, the steeping is carried out at a temperature of about 52° C. for a period of 22–50 hours, so it is desirable that the thioredoxin is stable under these conditions.

The grain may be a dicotyledonous seed, for example, an oil seed, e.g., soybean, sunflower or canola, preferably soybean; or may be a monocotyledonous seed, for example a cereal seed, e.g., corn, wheat, oats, barley, rye or rice, most preferably corn.

The thioredoxin may be any protein bearing thiol groups which can be reversibly oxidized to form disulfide bonds and reduced by NAPDH in the presence of a thioredoxin reductase. Preferably the thioredoxin is derived from a thermophilic organism, as described above.

Thioredoxin and/or thioredoxin reductase for use in the instant invention is suitably produced in an engineered microbe, e.g. a yeast or aspergilles, or in an engineered plant capable of very high expression, e.g. in barley, e.g., under control of a promoter active during malting, such as a high pI alpha-amylase promoter or other gibberellin dependent promoter. The thioredoxin (in excreted or extracted form or in combination with the producer organism or parts thereof) is then added to the steepwater.

As an alternative or supplement to adding the thioredoxin to the steepwater, the enzyme can be expressed directly in the seed that is to be milled. Preferably, the enzyme is expressed during grain maturation or during a conditioning process.

Accordingly, in a further embodiment, the invention provides a method of making thioredoxin on an industrial scale in a transgenic organism, e.g., a plant, e.g., a cereal, such as barley or corn, or a microorganism, e.g., a yeast or aspergillis, for example a method comprising the steps of cultivating a transgenic organism having a chimeric gene which expresses thioredoxin, and optionally isolating or extracting the thioredoxin;

A method of using transgenic plants that produce elevated quantities of thioredoxin during seed maturation or germination such that the quality of the proteins in that seed are affected by the endogenously synthesized thioredoxin during seed development, or during the steeping process, thereby eliminating or reducing the need for conditioning with exogenous chemicals or enzymes prior to milling;

A method of making transgenic plants that produce elevated quantities of thioredoxin during seed maturation or germination such that the quality of the proteins in that seed are affected by the thioredoxin during seed development or during the steeping process, thereby eliminating or reducing the need for conditioning with exogenous chemicals or enzymes prior to milling.

A method for milling grain that uses transgenic seed containing thioredoxin, that results in higher starch and soluble protein yields.

The invention further comprises a transgenic organism having in its genome a chimeric expression cassette comprising a coding region encoding a thermostable thioredoxin or thioredoxin reductase under operative control of a promoter.

Preferably, the transgenic organism is a plant which expresses a thioredoxin and/or thioredoxin reductase in a form not naturally occurring in plants of that species or which expresses thioredoxin at higher levels than naturally occur in a plant of that species. Preferably, the thioredoxin is expressed in the seed during seed development, and is therefore preferably under control of a seed specific promoter. Optionally, expression of the thioredoxin is placed under control of an inducible or transactivator-regulated promoter, so that expression is activated by chemical induction or hybridization with a transactivator when desired. The thioredoxin is suitably targeted to the vacuoles of the plant by fusion with a vacuole targeting sequence.

In the present invention, thioredoxin coding sequences are fused to promoters active in plants and transformed into the nuclear genome or the plastid genome. The promoter is preferably a seed specific promoter such as the gamma-zein promoter. The promoter may alternatively be a chemically-inducible promoter such as the tobacco PR-1a promoter; or may be a chemically induced transactivator regulated promoter wherein the transactivator is under control of a chemically induced promoter; however, in certain situations, constitutive promoters such as the CaMV 35S or Gelvin promoter may be used. With a chemically inducible promoter, expression of the thioredoxin genes transformed into plants may be activated at an appropriate time by foliar application of a chemical inducer.

Alternatively, the thioredoxin coding sequence is under control of a transactivator regulated promoter, and expression is achieved by crossing the plant transformed with this sequence with a second plant expressing the transactivator. In a preferred form of this method, the first plant containing the thioredoxin coding sequence is the seed parent and is male sterile, while the second plant expressing the transactivator is the pollinator. Expression of thioredoxin in seeds is achieved by interplanting the first and second plants, e.g., such that the first plant is pollinated by the second and thioredoxin is expressed in the seeds of the first plant by activation of the transactivator regulated promoter with the transactivator expressed by the transactivator gene from the second parent.

The nucleic acid sequences described in this application can be incorporated into plant cells using conventional recombinant DNA technology. Generally, this involves inserting a coding sequence of the invention into an expression system to which the coding sequence is heterologous (i.e., not normally present) using standard cloning procedures known in the art. The vector contains the necessary elements for the transcription and translation of the inserted protein-coding sequences. A large number of vector systems known in the art can be used, such as plasmids, bacteriophage viruses and other modified viruses. Suitable vectors include, but are not limited to, viral vectors such as lambda vector systems λgt11, λgt10 and Charon 4; plasmid vectors such as pBI121, pBR322, pACYC177, pACYC184, pAR series, pKK223-3, pUC8, pUC9, pUC18, pUC19, pLG339, pRK290, pKC37, pKC101, pCDNAII; and other similar systems. The components of the expression system may also be modified to increase expression. For example, truncated sequences, nucleotide substitutions or other modifications may be employed. The expression systems described herein can be used to transform virtually any crop plant cell under suitable conditions. Transformed cells can be regenerated into whole plants such that the nucleotide sequence of the invention is expressed in the transgenic plants.

Modification of Coding Sequences and Adjacent Sequences

The transgenic expression in plants of genes derived from microbial sources may require the modification of those genes to achieve and optimize their expression in plants. In particular, bacterial ORFs which encode separate enzymes but which are encoded by the same transcript in the native microbe are best expressed in plants on separate transcripts. To achieve this, each microbial ORF is isolated individually and cloned within a cassette which provides a plant promoter sequence at the 5' end of the ORF and a plant transcriptional terminator at the 3' end of the ORF. The isolated ORF sequence preferably includes the initiating ATG codon and the terminating STOP codon but may include additional sequence beyond the initiating ATG and the STOP codon. In addition, the ORF may be truncated, but still retain the required activity; for particularly long ORFs, truncated versions which retain activity may be preferable for expression in transgenic organisms. By "plant promoter" and "plant transcriptional terminator" it is intended to mean promoters and transcriptional terminators which operate within plant cells. This includes promoters and transcription terminators which may be derived from non-plant sources such as viruses (an example is the Cauliflower Mosaic Virus).

In some cases, modification to the ORF coding sequences and adjacent sequence is not required. It is sufficient to isolate a fragment containing the ORF of interest and to insert it downstream of a plant promoter. For example, Gaffney et al. (Science 261: 754–756 (1993)) have expressed the Pseudonionas nahG gene in transgenic plants under the control of the CaMV 35S promoter and the CaMV tml terminator successfully without modification of the coding sequence and with x bp of the Pseudomonas gene upstream of the ATG still attached, and y bp downstream of the STOP codon still attached to the nahG ORF. Preferably as little adjacent microbial sequence should be left attached upstream of the ATG and downstream of the STOP codon. In practice, such construction may depend on the availability of restriction sites.

In other cases, the expression of genes derived from microbial sources may provide problems in expression. These problems have been well characterized in the art and are particularly common with genes derived from certain sources such as Bacillus. These problems may apply to the nucleotide sequence of this invention and the modification of these genes can be undertaken using techniques now well known in the art. The following problems may be encountered:

1. Codon Usage.

The preferred codon usage in plants differs from the preferred codon usage in certain microorganisms. Comparison of the usage of codons within a cloned microbial ORF to usage in plant genes (and in particular genes from the target plant) will enable an identification of the codons within the ORF which should preferably be changed. Typically plant evolution has tended towards a strong preference of the nucleotides C and G in the third base position of monocotyledons, whereas dicotyledons often use the nucleotides A or T at this position. By modifying a gene to incorporate preferred codon usage for a particular target transgenic species, many of the problems described below for GC/AT content and illegitimate splicing will be overcome.

2. GC/AT Content.

Plant genes typically have a GC content of more than 35%. ORF sequences which are rich in A and T nucleotides can cause several problems in plants. Firstly, motifs of ATTTA are believed to cause destabilization of messages and are found at the 3' end of many short-lived mRNAs. Secondly, the occurrence of polyadenylation signals such as AATAAA at inappropriate positions within the message is believed to cause premature truncation of transcription. In addition, monocotyledons may recognize AT-rich sequences as splice sites (see below).

3. Sequences Adjacent to the Initiating Methionine.

Plants differ from microorganisms in that their messages do not possess a defined ribosome binding site. Rather, it is believed that ribosomes attach to the 5' end of the message and scan for the first available ATG at which to start translation. Nevertheless, it is believed that there is a preference for certain nucleotides adjacent to the ATG and that expression of microbial genes can be enhanced by the inclusion of a eukaryotic consensus translation initiator at the ATG. Clontech (1993/1994 catalog, page 210, incorporated herein by reference) have suggested one sequence as a consensus translation initiator for the expression of the *E. coli* uida gene in plants. Further, Joshi (NAR 15: 6643–6653 (1987), incorporated herein by reference) has compared many plant sequences adjacent to the ATG and suggests another consensus sequence. In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. Preferred sequences adjacent to the initiating methionine may differ between different plant species. A survey of 14 maize genes located in the GenBank database provided the following results:

| Position Before the Initiating ATG in 14 Maize Genes: | | | | | | | | | | |
|---|---|---|---|---|---|---|---|---|---|---|
| | -10 | -9 | -8 | -7 | -6 | -5 | -4 | -3 | -2 | -1 |
| C | 3 | 8 | 4 | 6 | 2 | 5 | 6 | 0 | 10 | 7 |
| T | 3 | 0 | 3 | 4 | 3 | 2 | 1 | 1 | 1 | 0 |
| A | 2 | 3 | 1 | 4 | 3 | 2 | 3 | 7 | 2 | 3 |
| G | 6 | 3 | 6 | 0 | 6 | 5 | 4 | 6 | 1 | 5 |

This analysis can be done for the desired plant species into which the nucleotide sequence is being incorporated, and the sequence adjacent to the ATG modified to incorporate the preferred nucleotides.

4. Removal of Illegitimate Splice Sites.

Genes cloned from non-plant sources and not optimized for expression in plants may also contain motifs which may be recognized in plants as 5' or 3' splice sites, and be cleaved, thus generating truncated or deleted messages. These sites can be removed using the techniques well known in the art.

Techniques for the modification of coding sequences and adjacent sequences are well known in the art. In cases where the initial expression of a microbial ORF is low and it is deemed appropriate to make alterations to the sequence as described above, then the construction of synthetic genes can be accomplished according to methods well known in the art. These are, for example, described in the published patent disclosures EP 0 385 962 (to Monsanto), EP 0 359 472 (to Lubrizol) and WO 93/07278 (to Ciba-Geigy), all of which are incorporated herein by reference. In most cases it is preferable to assay the expression of gene constructions using transient assay protocols (which are well known in the art) prior to their transfer to transgenic plants.

Construction of Plant Expression Cassettes

Coding sequences intended for expression in transgenic plants are first assembled in expression cassettes behind a suitable promoter expressible in plants. The expression cassettes may also comprise any further sequences required or selected for the expression of the transgene. Such sequences include, but are not restricted to, transcription terminators, extraneous sequences to enhance expression such as introns, vital sequences, and: sequences intended for the targeting of the gene product to specific organelles and cell compartments. These expression cassettes can then be easily transferred to the plant transformation vectors described below. The following is a description of various components of typical expression cassettes.

1. Promoters

The selection of the promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and the selection will reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters can be used, including the gene's native promoter. The following are non-limiting examples of promoters that may be used in expression cassettes.

a. Constitutive Expression, the Ubiquitin Promoter:

Ubiquitin is a gene product known to accumulate in many cell types and its promoter has been cloned from several species for use in transgenic plants (e.g. sunflower—Binet et al. Plant Science 79: 87–94 (1991); maize—Christensen et al. *Plant Molec. Biol.* 12: 619–632 (1989); and Arabidopsis—Norris et al., *Plant Mol. Biol.* 21:895–906 (1993)). The maize ubiquitin promoter has been developed in transgenic monocot systems and its sequence and vectors constructed for monocot transformation are disclosed in the patent publication EP 0 342 926 (to Lubrizol) which is herein incorporated by reference. Taylor et al. (Plant Cell Rep. 12: 491–495 (1993)) describe a vector (pAHC25) that comprises the maize ubiquitin promoter and first intron and its high activity in cell suspensions of numerous monocotyledons when introduced via microprojectile bombardment. The Arabidopsis ubiquitin promoter is ideal for use with the nucleotide sequences of the present invention. The ubiquitin promoter is suitable for gene expression in transgenic plants, both monocotyledons and dicotyledons. Suitable vectors are derivatives of pAHC25 or any of the transformation vectors described in this application, modified by the introduction of the appropriate ubiquitin promoter and/or intron sequences.

b. Constitutive Expression, the CaMV 35S Promoter:

Construction of the plasmid pCGN1761 is described in the published patent application EP 0 392 225 (Example 23), which is hereby incorporated by reference. pCGN1761 contains the "double" CaMV 35S promoter and the tml transcriptional terminator with a unique EcoRI site between the promoter and the terminator and has a pUC-type backbone. A derivative of pCGN1761 is constructed which has a modified polylinker which includes NotI and XhoI sites in addition to the existing EcoRI site. This derivative is designated pCGN1761ENX. pCGN1761ENX is useful for the cloning of cDNA sequences or coding sequences (including microbial ORF sequences) within its polylinker for the purpose of their expression under the control of the 35S promoter in transgenic plants. The entire 35S promoter-coding sequence-tml terminator cassette of such a construction can be excised by HindIII, SphI, SalI, and XbaI sites 5' to the promoter and XbaI, BamHI and BglI sites 3' to the terminator for transfer to transformation vectors such as those described below. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter. If desired, modifications around the cloning sites can be made by the introduction of sequences that may enhance translation. This is particularly useful when overexpression is desired. For example, pCGN1761ENX may be modified by optimization of the translational initiation site as described in Example 37 of U.S. Pat. No. 5,639,949, incorporated herein by reference.

c. Constitutive Expression, the Actin Promoter:

Several isoforms of actin are known to be expressed in most cell types and consequently the actin promoter is a good choice for a constitutive promoter. In particular, the promoter from the rice ActI gene has been cloned and characterized (McElroy et al. Plant Cell 2: 163–171 (1990)). A 1.3 kb fragment of the promoter was found to contain all the regulatory elements required for expression in rice protoplasts. Furthermore, numerous expression vectors based on the ActI promoter have been constructed specifically for use in monocotyledons (McElroy et al. Mol. Gen. Genet. 231: 150–160 (1991)). These incorporate the ActI-intron 1, AdhI 5' flanking sequence and AdhI-intron 1 (from the maize alcohol dehydrogenase gene) and sequence from the CaMV 35S promoter. Vectors showing highest expression were fusions of 35S and ActI intron or the ActI 5' flanking sequence and the ActI intron. Optimization of sequences around the initiating ATG (of the GUS reporter gene) also enhanced expression. The promoter expression cassettes described by McElroy et al. (Mol. Gen. Genet. 231: 150–160 (1991)) can be easily modified for gene expression and are particularly suitable for use in monocotyledonous hosts. For example, promoter-containing fragments is removed from the McElroy constructions and used to replace the double 35S promoter in pCGN1761ENX, which is then available for the insertion of specific gene sequences. The fusion genes thus constructed can then be transferred to appropriate transformation vectors. In a separate report, the rice ActI promoter with its first intron has also been found to direct high expression in cultured barley cells (Chibbar et al. Plant Cell Rep. 12: 506–509 (1993)).

d. Inducible Expression, the PR-1 Promoter:

The double 35S promoter in pCGN1761ENX may be replaced with any other promoter of choice that will result in suitably high expression levels. By way of example, one of the chemically regulatable promoters described in U.S. Pat. No. 5,614,395 may replace the double 35S promoter. The promoter of choice is preferably excised from its source by restriction enzymes, but can alternatively be PCR-amplified using primers that carry appropriate terminal restriction sites. Should PCR-amplification be undertaken, then the promoter should be re-sequenced to check for amplification errors after the cloning of the amplified promoter in the target vector. The chemically/pathogen regulatable tobacco PR-1a promoter is cleaved from plasmid pCIB 1004 (for construction, see example 21 of EP 0 332 104, which is hereby incorporated by reference) and transferred to plasmid pCGN1761ENX (Uknes et al., 1992). pCIB1004 is cleaved with NcoI and the resultant 3' overhang of the linearized fragment is rendered blunt by treatment with T4 DNA polymerase. The fragment is then cleaved with HindIII and the resultant PR-1a promoter-containing fragment is gel purified and cloned into pCGN1761ENX from which the double 35S promoter has been removed. This is done by cleavage with XhoI and blunting with T4 polymerase, followed by cleavage with HindIII and isolation of the larger vector-terminator containing fragment into which the pCIB 1004 promoter fragment is cloned. This generates a pCGN1761ENX derivative with the PR-1a promoter and the tml terminator and an intervening polylinker with unique EcoRI and NotI sites. The selected coding sequence can be inserted into this vector, and the fusion products (i.e. promoter-gene-terminator) can subsequently be transferred to any selected transformation vector, including those described infra. Various chemical regulators may be employed to induce expression of the selected coding sequence in the plants transformed according to the present invention, including the benzothiadiazole, isonicotinic acid, and salicylic acid compounds disclosed in U.S. Pat. Nos. 5,523,311 and 5,614,395.

e. Inducible Expression, an Ethanol-Inducible Promoter:

A promoter inducible by certain alcohols or ketones, such as ethanol, may also be used to confer inducible expression of a coding sequence of the present invention. Such a promoter is for example the alcA gene promoter from *Aspergillus nidulans* (Caddick et al. (1998) *Nat. Biotechnol* 16:177–180). In *A. nidulans*, the alcA gene encodes alcohol dehydrogenase I, the expression of which is regulated by the AlcR transcription factors in presence of the chemical inducer. For the purposes of the present invention, the CAT coding sequences in plasmid palcA:CAT comprising a alcA gene promoter sequence fused to a minimal 35S promoter (Caddick et al. (1998) *Nat. Biotechnol* 16:177–180) are replaced by a coding sequence of the present invention to form an expression cassette having the coding sequence under the control of the alcA gene promoter. This is carried out using methods well known in the art.

f. Inducible Expression, a Glucocorticoid-Inducible Promoter:

Induction of expression of a nucleic acid sequence of the present invention using systems based on steroid hormones is also contemplated. For example, a glucocorticoid-mediated induction system is used (Aoyama and Chua (1997) *The Plant Journal* 11: 605–612) and gene expression is induced by application of a glucocorticoid, for example a synthetic glucocorticoid, preferably dexamethasone, preferably at a concentration ranging from 0.1 mM to 1 mM, more preferably from 10 mM to 100 mM. For the purposes of the present invention, the luciferase gene sequences are replaced by a nucleic acid sequence of the invention to form an expression cassette having a nucleic acid sequence of the invention under the control of six copies of the GAL4 upstream activating sequences fused to the 35S minimal promoter. This is carried out using methods well known in the art. The trans-acting factor comprises the GAL4 DNA-binding domain (Keegan et al. (1986) *Science* 231: 699–704) fused to the transactivating domain of the herpes viral protein VP16 (Triezenberg et al. (1988) *Genes Devel.* 2: 718–729) fused to the hormone-binding domain of the rat glucocorticoid receptor (Picard et al. (1988) *Cell* 54: 1073–1080). The expression of the fusion protein is controlled by any promoter suitable for expression in plants known in the art or described here. This expression cassette is also comprised in the plant comprising a nucleic acid sequence of the invention fused to the 6×GAL4/minimal promoter. Thus, tissue- or organ-specificity of the fusion protein is achieved leading to inducible tissue- or organ-specificity of the insecticidal toxin.

g. Root Specific Expression:

Another pattern of gene expression is root expression. A suitable root promoter is described by de Framond (FEBS 290: 103–106 (1991)) and also in the published patent application EP 0 452 269, which is herein incorporated by reference. This promoter is transferred to a suitable vector such as pCGN1761ENX for the insertion of a selected gene and subsequent transfer of the entire promoter-gene-terminator cassette to a transformation vector of interest.

h. Wound-Inducible Promoters:

Wound-inducible promoters may also be suitable for gene expression. Numerous such promoters have been described (e.g. Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al.

Plant Molec. Biol. 22: 129–142 (1993), Warner et al. Plant J. 3: 191–201 (1993)) and all are suitable for use with the instant invention. Logemann et al. describe the 5' upstream sequences of the dicotyledonous potato wuni gene. Xu et al. show that a wound-inducible promoter from the dicotyledon potato (pin2) is active in the monocotyledon rice. Further, Rohrmeier & Lehle describe the cloning of the maize WipI cDNA which is wound induced and which can be used to isolate the cognate promoter using standard techniques. Similar, Firek et al. and Warner et al. have described a wound-induced gene from the monocotyledon *Asparagus officinalis*, which is expressed at local wound and pathogen invasion sites. Using cloning techniques well known in the art, these promoters can be transferred to suitable vectors, fused to the genes pertaining to this invention, and used to express these genes at the sites of plant wounding.

Pith-Preferred Expression:

Patent Application WO 93/07278, which is herein incorporated by reference, describes the isolation of the maize trpA gene, which is preferentially expressed in pith cells.: The gene sequence and promoter extending up to −1726 bp from the start of transcription are presented. Using standard molecular biological techniques, this promoter, or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

j. Leaf-Specific Expression:

A maize gene encoding phosphoenol carboxylase (PEPC) has been described by Hudspeth & Grula (Plant Molec Biol 12: 579–589 (1989)). Using standard molecular biological techniques the promoter for this gene can be used to drive the expression of any gene in a leaf-specific manner in transgenic plants.

k. Pollen-Specific Expression:

WO 93/07278 describes the isolation of the maize calcium-dependent protein kinase (CDPK) gene which is expressed in pollen cells. The gene sequence and promoter extend up to 1400 bp from the start of transcription. Using standard molecular biological techniques, this promoter or parts thereof, can be transferred to a vector such as pCGN1761 where it can replace the 35S promoter and be used to drive the expression of a nucleic acid sequence of the invention in a pollen-specific manner.

2. Transcriptional Terminators

A variety of transcriptional terminators are available for use in expression cassettes. These are responsible for the termination of transcription beyond the transgene and its correct polyadenylation. Appropriate transcriptional terminators are those that are known to function in plants and include the CaMV 35S terminator, the tml terminator, the nopaline synthase terminator and the pea rbcS E9 terminator. These can be used in both monocotyledons and dicotyledons. In addition, a gene's native transcription terminator may be used.

3. Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adhl gene have been found to significantly enhance the expression of the wild-type gene under its cognate promoter when introduced into maize cells. Intron I was found to be particularly effective and enhanced expression in fusion constructs with the chloramphenicol acetyltransferase gene (Callis et al., Genes Develop. 1: 1183–1200 (1987)). In the same experimental system, the intron from the maize bronzel gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. *Nucl. Acids Res.* 15: 8693–8711 (1987); Skuzeski et al. Plant Molec. Biol. 15: 65–79 (1990)).

4. Targeting of the Gene Product Within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. J. Biol. Chem. 263: 15104–15109 (1988)). These signal sequences can be fused to heterologous gene products to effect the import of heterologous products into the chloroplast (van den Broeck, et al. Nature 313: 358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized. See also, the section entitled "Expression With Chloroplast Targeting" in Example 37 of U.S. Pat. No. 5,639,949.

Other gene products are localized to other organelles such as the mitochondrion and the peroxisome (e.g. Unger et al. Plant Molec. Biol. 13: 411–418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting cellular protein bodies has been described by Rogers et al. (Proc. Natl. Acad. Sci. USA 82: 6512–6516 (1985)).

In addition, sequences have been characterized which cause the targeting of gene products to other cell compartments. Amino terminal sequences are responsible for targeting to the ER, the apoplast, and extracellular secretion from aleurone cells (Koehler & Ho, Plant Cell 2: 769–783 (1990)). Additionally, amino terminal sequences in conjunction with carboxy terminal sequences are responsible for vacuolar targeting of gene products (Shinshi et al. Plant Molec. Biol. 14: 357–368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site, and the fusion constructed should take into account any amino acids after the cleavage site which are required for cleavage. In some cases this requirement may be fulfilled by the addition of a small number of amino acids between the cleavage site and the transgene ATG or, alternatively, replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by Bartlett et al. In: Edelmann et al. (Eds.). Methods in Chloroplast Molecular Biology, Elsevier pp 1081–1091 (1982) and Wasmann et al. Mol. Gen. Genet. 205: 446–453 (1986). These construction techniques are well known in the art and are equally applicable to mitochondria and peroxisomes.

The above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

Construction of Plant Transformation Vectors

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformnation include the nptII gene, which confers resistance to kanamycin and related antibiotics (Messing & Vierra. Gene 19: 259–268 (1982); Bevan et al., Nature 304:184–187 (1983)), the bar gene, which confers resistance to the herbicide phosphinothricin (White et al., Nucl. Acids Res 18: 1062 (1990), Spencer et al. Theor. Appl. Genet 79: 625–631 (1990)), the hph gene, which confers resistance to the antibiotic hygromycin (Blochinger & Diggelmann, Mol Cell Biol 4: 2929–2931), and the dhfr gene, which confers resistance to methatrexate (Bourouis et al., EMBO J. 2(7): 1099–1104 (1983)), the EPSPS gene, which confers resistance to glyphosate (U.S. Pat. Nos. 4,940,935 and 5,188,642), and the mannose-6-phosphate isomerase gene, which provides the ability to metabolize mannose (U.S. Pat. Nos. 5,767,378 and 5,994, 629).

1. Vectors Suitable for Agrobacterium Transformation

Many vectors are available for transformation using *Agrobacterium tumefaciens*. These typically carry at least one T-DNA border sequence and include vectors such as pBIN19 (Bevan, *Nucl. Acids Res.* (1984)) and pXYZ. Below, the construction of two typical vectors suitable for Agrobacterium transformation is described.

a. pCIB200 and pCIB2001:

The binary vectors pcIB200 and pCIB2001 are used for the construction of recombinant vectors for use with Agrobacterium and are constructed in the following manner. pTJS75kan is created by NarI digestion of pTJS75 (Schmidhauser & Helinski, J. Bacteriol. 164: 446–455 (1985)) allowing excision of the tetracycline-resistance gene, followed by insertion of an AccI fragment from pUC4K carrying an NPTII (Messing & Vierra, Gene 19: 259–268 (1982): Bevan et al., Nature 304: 184–187 (1983): McBride et al., Plant Molecular Biology 14: 266–276 (1990)). XhoI linkers are ligated to the EcoRV fragment of PCIB7 which contains the left and right T-DNA borders, a plant selectable nos/nptll chimeric gene and the pUC polylinker (Rothstein et al., Gene 53: 153–161 (1987)), and the XhoI-digested fragment are cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200 created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for Agrobacterium-mediated transformation, the RK2-derived trfA function for mobilization between E. coli and other hosts, and the OriT and OriV functions also from RK2. The pCIB2001 polylinker is suitable for the cloning of plant expression cassettes containing their own regulatory signals.

b. pCIB10 and Hygromycin Selection Derivatives thereof:

The binary vector pCIB 10 contains a gene encoding kanamycin resistance for selection in plants and T-DNA right and left border sequences and incorporates sequences from the wide host-range plasmid pRK252 allowing it to replicate in both *E. coli* and Agrobacterium. Its construction is described by Rothstein et al. (Gene 53: 153–161 (1987)). Various derivatives of pCIB 10 are constructed which incorporate the gene for hygromycin B phosphotransferase described by Gritz et al. (Gene 25: 179–188 (1983)). These derivatives enable selection of transgenic plant cells on hygromycin only (pCIB743), or hygromycin and kanamycin (pCIB715, pCIB717).

2. Vectors Suitable for non-Agrobacterium Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on Agrobacterium include transformation via particle bombardment, protoplast uptake (e.g. PEG and electroporation) and microinjection. The choice of vector depends largely on the preferred selection for the species being transformed. Below, the construction of typical vectors suitable for non-Agrobacterium transformation is described.

a. pCIB3064:

pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites are mutated using standard PCR techniques in such a way as to remove the ATGs and generate the restriction sites SspI and PvuII. The new restriction sites are 96 and 37 bp away from the unique SalI site and 101 and 42 bp away from the actual start site. The resultant derivative of pCIB246 is designated pCIB3025. The GUS gene is then excised from pCIB3025 by digestion with SalI and SacI, the termini rendered blunt and religated to generate plasmid pCIB3060.

The plasmid pJIT82 is obtained from the John Innes Centre, Norwich and the a 400 bp SmaI fragment containing the bar gene from *Streptomyces viridochromogenes* is excised and inserted into the HpaI site of pCIB3060 (Thompson et al. EMBO J 6: 2519–2523 (1987)). This generated pCIB3064, which comprises the bar gene under the control of the CaMV 35S promoter and terminator for herbicide selection, a gene for ampicillin resistance (for selection in *E. coli*) and a polylinker with the unique sites :SphI, PstI, HindIII, and BanHI. This vector is suitable for the cloning of plant expression cassettes containing their own regulatory signals.

b. pSOG19 and pSOG35:

pSOG35 is a transformation vector that utilizes the *E. coli* gene dihydrofolate reductase (DFR) as a selectable marker conferring resistance to methotrexate. PCR is used to amplify the 35S promoter (–800 bp), intron 6 from the maize Adhl gene (–550 bp) and 18 bp of the GUS untranslated leader sequence from pSOG10. A 250-bp fragment encoding the *E. coli* dihydrofolate reductase type II gene is also amplified by PCR and these two PCR fragments are assembled with a SacI-PstI fragment from pB1221 (Clontech) which comprises the pUC19 vector backbone and the nopaline synthase terminator. Assembly of these fragments generates pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have HindIII, SphI, PstI and EcoRI sites available for the cloning of foreign substances.

3. Vector Suitable for Chloroplast Transformation

For expression of a nucleotide sequence of the present invention in plant plastids, plastid transformation vector pPH143 (WO 97/32011, example 36) is used. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

Transformation

Once a nucleic acid sequence of the invention has been cloned into an expression system, it is transformed into a plant cell. Methods for transformation and regeneration of plants are well known in the art. For example, Ti plasmid vectors have been utilized for the delivery of foreign DNA, as well as direct DNA uptake, liposomes, electroporation, micro-injection, and microprojectiles. In addition, bacteria from the genus Agrobacterium can be utilized to transform plant cells. Below are descriptions of representative techniques for transforming both dicotyledonous and monocotyledonous plants, as well as a representative plastid transformation technique.

1. Transformation of Dicotyledons

Transformation techniques for dicotyledons are well known in the art and include Agrobacterium-based techniques and techniques that do not require Agrobacterium. Non-Agrobacterium techniques involve the uptake of exogenous genetic material directly by protoplasts or cells. This can be accomplished by PEG or electroporation mediated uptake, particle bombardment-mediated delivery, or micro-injection. Examples of these techniques are described by Paszkowski et al., EMBO J 3: 2717–2722 (1984), Potrykus et al., Mol. Gen. Genet. 199: 169–177 (1985), Reich et al., Biotechnology 4: 1001–1004 (1986), and Klein et al., Nature 327: 70–73 (1987). In each case the transformed cells are regenerated to whole plants using standard techniques known in the art.

Agrobacterium-mediated transformation is a preferred technique for transformation of dicotyledons because of its high efficiency of transformation and its broad utility with many different species. Agrobacterium transformation typically involves the transfer of the binary vector carrying the foreign DNA of interest (e.g. pCIB200 or pCIB2001) to an appropriate Agrobacterium strain which may depend of the complement of vir genes carried by the host Agrobacterium strain either on a co-resident Ti plasmid or chromosomally (e.g. strain CIB542 for pCIB200 and pCIB2001 (Uknes et al. Plant Cell 5: 159–169 (1993)). The transfer of the recombinant binary vector to Agrobacterium is accomplished by a triparental mating procedure using *E. coli* carrying the recombinant binary vector, a helper *E. coli* strain which carries a plasmid such as pRK2013 and which is able to mobilize the recombinant binary vector to the target Agrobacterium strain. Alternatively, the recombinant binary vector can be transferred to Agrobacterium by DNA transformation (Höfgen & Willmitzer, Nucl. Acids Res. 16: 9877 (1988)).

Transformation of the target plant species by recombinant Agrobacterium usually involves co-cultivation of the Agrobacterium with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

2. Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093–1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603–618 (1990)) and Fromm et al. (Biotechnology 8: 833–839 (1990)) have published techniques for transformation of A188-derived maize line using particle bombardment. Furthermore, WO 93/07278 and Koziel et al. (Biotechnology 11: 194–200 (1993)) describe techniques for the transformation of elite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. Plant Cell Rep 7: 379–384 (1988); Shimamoto et al. Nature 338: 274–277 (1989); Datta et al. Biotechnology 8: 736–740 (1990)). Both types are also routinely transformable using particle bombardment (Christou et al. Biotechnology 2: 957–962 (1991)). Furthermore, WO 93/21335 describes techniques for the transformation of rice via electroporation.

Patent Application EP 0 332 581 describes techniques for the generation, transformation and regeneration of Pooideae protoplasts. These techniques allow the transformation of Dactylis and wheat. Furthermore, wheat transformation has been described by Vasil et al. (Biotechnology 10: 667–674 (1992)) using particle bombardment into cells of type C long-term regenerable callus, and also by Vasil et al. (Biotechnology 11: 1553–1558 (1993)) and Weeks et al. (Plant Physiol. 102: 1077–1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashiga & Skoog, Physiologia Plantarum 15: 473–497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Tranformation of monocotyledons using Agrobacterium has also been described. See, WO 94/00977 and U.S. Pat. No. 5,591,616, both of which are incorporated herein by reference.

3. Transformation of Plastids

In another preferred embodiment, a nucleotide sequence of the present invention is directly transformed into the plastid genome. A major advantage of plastid transformation is that plastids are generally capable of expressing bacterial genes without substantial modification, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) Proc. Natl. Acad. Sci. USA 91, 7301–7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Natl. Acad. Sci. USA 87, 8526–8530; Staub, J. M., and Maliga, P. (1992) Plant Cell 4, 39–45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) EMBO J. 12, 601–606). Substantial increases in transformation frequency are obtained by replacement of the recessive rRNA or r-protein antibiotic resistance genes with a dominant selectable marker, the bacterial aada gene encoding the spectinomycin-detoxifying enzyme aminoglycoside-3'-adenyltransferase (Svab, Z., and Maliga, P. (1993) Proc. Natl. Acad. Sci. USA 90, 913–917). Previously, this marker had been used successfully for high-frequency transformation of the plastid genome of the green alga Chliamydomonas reinhardtii (Goldschmidt-Clermont, M. (1991) Nucl. Acids Res. 19: 4083–4089). Other selectable markers useful for plastid transformation are known in the art and encompassed within the scope of the invention. Typically, approximately 15–20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleotide sequence of the present invention is inserted into a plastid targeting vector and transformed into the plastid genome of a desired plant host. Plants homoplastic for plastid genomes containing a nucleotide sequence of the present invention are obtained, and are preferentially capable of high expression of the nucleotide sequence.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989); and by T. J. Silhavy, M. L. Berman, and L. W. Enquist, Experiments with Gene Fusions, Cold Spring Harbor Laboratory, Cold Spring Harbor, N.Y. (1984).

Example 1

Transformation of Maize with Heat-stable Thioredoxin

A gene expressing the heat-stable thioredoxin from *Methanococcus jannaschii*, having the sequence shown in SEQ ID NO:1 is prepared using maize preferred codons as described in U.S. Pat. No. 5,625,136, under control of the seed-specific gamma-zein promotor, and the expression cassette incorporated between the T-DNA boundried of the pGIGUP plasmid.

Strain *Agrobacterium tumefaciens* LBA4404 (pAL4404, pSB1) is used in these experiments. pALA4404 is a disarmed helper plasmid. pSB1 is a wide host range plasmid that contains a region of homology to pGIGUP and a 15.2 kb KpnI fragment from the virulence region of pTiBo542 (Ishida et al., 1996; High efficiency transformation of maize (Zea mays L.) mediated by *Agrobacterium tumefaciens*, Nature Biotechnology 14, 745–750). The introduction of the plasmid pGIGUP by electroporation into LBA4404 (pAL4404, pSB1) results in a cointegration of pGIGUP and pSB1. The T-DNA of this plasmid contains a mannose-6-phosphate isomerase gene driven by the ubiquitin promoter to provide the ability to metabolize mannose, as well as the thioredoxin gene described above.

Agrobacterium is grown for 3 days on YP medium (5 g/l yeast extract, 10 g/l peptone, 5 g/l NaCl, 15 g/l agar, pH 6.8) supplemented with 50 mg/l spectinomycin and 10 mg/l tetracycline. Bacteria are collected with a loop and suspended in N6 liquid medium at a density ranging from $10^9$ to $5\ 10^9$ cells/ml. Agrobacterium cells can also be collected from an overnight culture in YP medium and resuspended in N6 liquid medium.

Maize immature embryos are obtained approximately 10 to 14 days after self-pollination. The immature zygotic embryos are divided among different plates containing medium capable of inducing and supporting embryogenic callus formation at about 25 immature embryos per plate.

The immature embryos are inoculated either on the plate or in liquid with Agrobacterium having a Ti plasmid comprising a selectable marker gene. The immature embryos are plated on callus initiation medium containing silver nitrate (10 mg/l) either prior or immediately after inoculation with Agrobacterium. Approximately 25 immature embryos are placed onto each plate. 16 to 72 hours after inoculation, immature embryos are transferred to callus initiation medium with silver nitrate and cefotaxim. Selection of transformed cells is carried out as follows: Mannose is used to select transformed cells in vitro. This selection can be applied as low as 1 g/l 2 to 20 days after inoculation and maintained for a total of 2–12 weeks. The embryogenic callus so obtained is regenerated in the presence or absence of mannose on standard medium of regeneration. All plants are tested by the chlorophenol red (CR) test for tolerance to mannose. This assay utilizes a pH sensitive indicator dye to show which cells are growing in the presence of mannose. Cells that grow produce a pH change in the media and turn the indicator Chlorophenol Red yellow from red. Plants expressing the tolerance to mannose are easily identified in this test. Plants positive by the CR test are assayed by PCR for the presence of the mannose gene. Plants which are positive for PCR test are analyzed by Southern blot.

The regenerated plants are assayed for expression of the thioredoxin. The plants are developmentally normal. Corn grain from progeny plants derived from the highest expressing event is assayed in a small scale wet milling process and starch extractability is measured compared to corn of the same genotype without the thioredoxin transgene. Corn expressing the thioredoxin gene exhibits substantially greater starch availability in the wet milling process than the isogenic non-transformed corn.

Example 2

Transformation of Maize with Heat-stable Thioredoxin and Thioredoxin Reductase Using the procedures described in Example 1, maize is co-transformed with genes encoding both thioredoxin (SEQ ID NO:1) and thioredoxin reductase (SEQ ID NO:6) from *Methanococcus jannaschii*. Both genes are under control of the seed specific gamma zein promoter. The two genes are linked and placed between the right and left borders of the pGIGUP plasmid to enhance the likelihood that both genes will be incorporated into the chromosome of the plant as a single insert.

The regenerated plants are assayed for expression of the thioredoxin and thioredoxin reductase. The plants are developmentally normal. Corn grain from progeny plants derived from the highest expressing event is assayed in a small scale wet milling process and starch extractability is measured compared to corn of the same genotype without the thioredoxin/thioredoxin reductase transgenes. Corn expressing the thioredoxin and thioredoxin reductase genes exhibits substantially greater starch availability in the wet milling process than the isogenic non-transformed corn.

Example 3

Cloning of Thioredoxin Genes and Construction of Plant Transforrnation Vectors Rice and wheat thioredoxin-h cDNA (trx-h) are cloned by RT-PCR using total RNA from rice and wheat germinated seeds, respectively. Amplification of trx cDNA is obtained by using primers NMD109-(5'-GGA TCC ACC ATG GCC GCC GAG GAG-3' (SEQ ID NO:8)) and NMD110 (5'-GAG CTC TTA GGC AGA AGC AGA TG-3' (SEQ ID NO:9)) for rice and NMD102 (5'-GGA TCC ACC ATG GCG GCG TCG G-3 (SEQ ID NO:10)) and NMD103 (5'-GAG CTC TTA CTG GGC CGC GTG T-3' (SEQ ID NO:11)) for wheat. Insertion of appropriate restriction sites required for cloning the gene into plant expression vectors viz., BamHI at the 5' end and SacI at the 3' end is also achieved with this reaction. PCR products of the correct size are gel purified and cloned using the Topo PCR 2.1 cloning vector (Invitrogen). Colonies containing the correct insert are sequenced following restriction analysis. The rice trx sequence matches that published in Genbank Accession no. U92541. The wheat cDNA sequence matches trx-h from *T. aestivium* (Genbank Accession No. X69915)

Cloning of the γ zein promoter: 673 bp γ zein promoter is amplified from plasmid pGZ27.3 obtained from Dr. Brian Larkins. This sequence also exactly matches the: opaque2 modifier 5' region (Genbank accession no. S78780) as well as (Marzabal et al. 1998. Plant J. 16:41–52). The γ zein promoter has been shown to be endosperm specific (Torrent et al. (1997) Plant Mol. Biol. 34: 139–149).

pNOV 3401: Maize ubiquitin promoter plus intron-rice trx-h-35S terminator in an Agrobacterium transformation vector with PMI selection:

Rice trx gene is cloned into a plant expression vector containing the maize ubiquitin promoter plus intron and a 35S terminator. The resulting construct pNOV 3400 is digested with restriction endonucleases HindIII and KpnI to subclone into an Agrobacterium transformation binary vector cassette pNOV 2117 to obtain pNOV 3401.

pNOV 3405: γ zein promoter-rice trx-h-35S terminator in an Agrobacterium transformation vector with PMI selection:

pNOV 3406: γ zein promoter-wheat trx-h-35S terminator in an Agrobacterium transformation vector with PMI selection:

Both rice and wheat trx-h genes are cloned into a plant expression vector containing the γ zein promoter described above and a 35S terminator. The resulting constructs are digested with HindIII, and KpnI to obtain the promoter, gene, terminator units and subcloned into an Agrobacterium binary vector pNOV 2117 resulting in pNOV 3405 and pNOV3406 respectively. pNOV 2117 is a binary vector with the gene for phosphomannose isomerase (PMI) driven by a maize ubiquitin promoter plus intron and a NOS terminator.

pNOV: 3408: γ zein promoter-γzein signal sequence-Rice trx-h-γ zein 3' end-35S terminator in an Agrobacterium transformation vector with PMI selection:

To target rice thioredoxin to the endomembrane system of the cell, signal sequences from the N-terminus and C-terminus of the γ-zein gene are used (Torrent et al. (1994) Planta 192: 512–518). Restriction sites Eco47AIII is inserted at the 5' end of the rice thioredoxin gene after the first ATG and restriction site NheI is inserted at the 3' end by PCR mutagenesis using mutagenic primers NMD124A (5''- GAGCTCTTAG GCGCTAGCAG ATG-3' (SEQ ID NO:12)) and NMD125A (5'-GGATCCACC A GCGCTGCCGA-3' (SEQ ID NO:13)). All mutations are silent. The gene is cloned into a topo PCR2.1 vector and sequenced. The trx fragment is obtained by digestion with restriction enzymes Eco47III and NheI. Four oligonucleotides are made to encode the γ zein signal sequence and the C- terminus: NMD126 (5'-GATCCACCAT GAGGGT-GTTG CTCGTFGCCC TCGCTCTCCT GGCTCTCGCT GCGAGCGCCA CCAGC-3' (SEQ ID NO:14)); NMD127 (5'-GCTGGTGGCG CTCGCAGCGA GAGCCAGGAG AGCGAGGGCA ACGAGCAACA CCCTCATGGT G-3' (SEQ ID NO:15)); NMD128 (5'-CTAGCGCTCT GCAG-CAGCCG ACTCCATGCC CCTACGCTGC TGCCG-GCGGT GTCCCCCACT GAGAGCT-3' (SEQ ID NO:16)); and NMD129 (5'-CTCAGTGGGG GACACCGCCG GCAGCAGCGT AGGGGCATGG AGTCGGCTGC TGCAGAGCG-3' (SEQ ID NO:17)). Oligo pairs NMD 126 and 127 and NMD 128 and 129 are hybridized and phosphorylated using T4 polynucleotide kinase following standard protocols. These two hybridized, kinased oligo pairs are ligated in a four-way ligation reaction with Eco47III, NheI digested trx described above and a plant expression vector cassette containing the γ zein promoter and 35S terminator. The resulting construct is digested with HindIII, and KpnI to obtain the promoter, gene, terminator unit and subcloned into an Agrobacterium binary vector pNOV 2117 containing the selectable marker phosphomannose isomerase (PMI) gene driven by a maize ubiquitin promoter, resulting in pNOV 3408.

pNOV 3401, pNOV3405, pNOV3406 and pNOV3408 are transformed into Agrobacterium strain LBA4404 (pSB1) and used for stable maize transformation.

Arabidopsis thioredoxin reductase is found to be active in reducing rice thioredoxin in vitro. Therefore a maize optimized NTR gene is constructed.

Example 4

Construction of a Maize Optimized Arabidopsis NADPH Dependent Thioredoxin Reductase Gene The Arabidopsis NADPH dependent thioredoxin reductase gene (NTR) is a 35kD protein. To design the synthetic gene, the deduced peptide sequence of the NTR gene (Genbank Accession # Z23109) is backtranslated using the "Backtranslation" program found in the University of Wisconsin GCG group of programs using a maize preference codon table (Murray et al. (1989) Nucl. Acids Res. 17: 477498). The "maize optimized" sequence is further modified to insert unique sites to facilitate cloning. The gene is designed to be cloned in three parts. Each fragment is constructed by hybridization of 8–10 pairs of oligomers 60–75 nucleotides in length representing. both strands of the gene. A 15 nucleotide overlap is designed between sequential oligo pairs for correct orientation and assembly. Oligos are synthesized by Genosys Inc., (Texas). Fragment 1 of the gene (corresponding to nucleotides 1–305) is constructed by amplifying the 305 bp fragment by PCR using Taq polymerase and the standard conditions recommended by the supplier, an equimolar mixture of 8 oligomers as template and primers STRF1A (5'-ggATCCACCA TgAACggCCT ggAg-3' (SEQ ID NO:18)) and STRF1B (5'-CTCgAgAAgT CCACCTTggT CAC-3' (SEQ ID NO:19)). The second fragment of the gene is constructed by amplifying a 346 bp fragment (nucleotides 299–645) by PCR using an equimolar mixture of 10 oligomers as template and primers STRF2A (5'-CTCgAgCAAg CCgTTCAA-3' (SEQ ID NO:20)) and STRF2B (5'-gACgTCgATC TTCgggTTgg A-3' (SEQ ID NO:21)). The third fragment of the gene is constructed by amplifying a 382 bp fragment (nucleotides 639–1021) by PCR using an equimolar mixture of 10 oligomers as template and primers STR3A (5'-CgACgTCATC TggAACTCCT-3' (SEQ ID NO:22)) and STR3B (5'-gAgCTCAgAT CTAgTCggAC TTg-3' (SEQ ID NO:23)). The amplified DNA for each fragment is cloned into a topo PCR2.1 T-vector (Invitrogen). Gene fragments with the correct sequence are joined using the overlapping restriction endonuclease site XhoI and AatII. The maize optimized Arabidopsis NADPH dependent thioredoxin reductase coding sequence is shown as SEQ ID NO:24 and the encoded amino acid sequence is shown as SEQ ID NO:25. The complete gene is constructed and sequenced and subcloned into plant expression vector cassette containing the γ zein promoter and 35S terminator. The promoter, gene, terminator unit is then subcloned into an Agrobacterium maize transformation vector alone and in conjunction with the rice and wheat thioredoxin genes.

Example 5

Rice NADPH Dependent Thioredoxin Reductase (NTR) Gene

The rice NADPH dependent thioredoxin reductase (NTR) coding sequence is shown as SEQ ID NO:26 and the corresponding amino acid sequence is shown as SEQ ID NO:27.

```
                              Aligned Sequences

Reference molecule: arab trPG (SEQ ID NO:25) 1 - 1002 (334 aa) Homology
Sequence 2:         TRCONAA.TXT (SEQ ID NO:27) 1 - 310 (310 aa) 70%
Alignment type:     Global Protein
Parameters:         Mismatch 2; Open Gap 4; Extend Gap 1; Conserv N arab trPG    (1)    mnglethn--
                    trlcivgsgpaahtaaiyaaraelkpllfegwmanandiapg
TRCONAA.TXT  (1)    .e.sagaplr.....i....s-
                    ...............v.....l........a.

arab trPG    (145)  gqlttttdvenfpgfpegilgveltdkfrkqserfgttiftetvtkvdfs
TRCONAA.TXT  (51)   ....................g..m.rc.a..l....s.is....a....

arab trPG    (295)  skpfklftdskailadavilaigavakwlsfvgsgevlgglwnrgisaca
TRCONAA.TXT  (101)  ar..rvas..ttv.....vv.t....rr.h.a..----day.........

arab trPG    (445)  vcdgaapifrnkplavigggdsameeanfltkygskvyiidrrdafrask
TRCONAA.TXT  (147)  ................i.............s........h....h..nt.....

arab trPG    (595)  imqqralsrpkidviwnssvveaygdgerdvlgglkvknvvtgdvsdlkv
TRCONAA.TXT  (197)  ...a........q.f.d.e......gegggp.a.v....l...ki...q.

arab trPG    (745)  sglffaighepatkfldggveldsdgyvvtkpgttqtsvpgvfaagdvqd
TRCONAA.TXT  (247)  ................g.ql...a....a.....s.h...k..........

arab trPG    (895)  kkyrqaitaagtgcmaaldaehylqeigsqqgksd*
TRCONAA.TXT  (297)  ...........------------------------.gl
```

Example 6

Alignment of Arabidopsis NTR and Rice Sequence Described Above

Example 7

Plant Transformation Vectors

PNOV4100-PTX5'-At PPO-35ST' and Ubq3 (At)-intron-NOS vector:

PBH28 (Arabidopsis Ubq3int-NOS) is digested with EcoRI, isolate 4756 bp band, fill-in with Kienow, ligate to pCTK2 (PTX5'-AtPPO-35ST) digest with HindIII-isolate 2386 bp band, fill-in with Klenow. pNOV 4100 contains PTX5', AtPPo,35ST',amp,Ubq3(At) intron NOS. Junctions are sequenced.

PNOV4101-β conglycinin α' subunit promoter-soybean thioredoxin-NOS in PPO vector pNOV4100:

Digest pNOV4100 with HindIII and SacI. Soybean β-conglycinin α' subunit promoter (Genbank accession # M13759) is cloned by PCR using soybean leaf genomic DNA and oligos P9 (5'-gac taa gct tac aat tat tat atc aaa atg gc-3' (SEQ ID NO:28)) and P10 (5'-gct ttt ccc aat acg caa tgc-3' (SEQ ID NO:29)) (Sylvain et al. (1992) Plant Mol. Biol. 19:937–949). This PCR product is cloned into pCR 2.1 TOPO vector and sequenced. This construct is used as template in PCR with oligos P4 (5'-gac tag cgc tga cag aaa ctg atg cta gga a-3' (SEQ ID NO:30)) and P9 (5'-gac taa gct tac aat tat tat atc aaa atg gc-3' (SEQ ID NO:28)). Digest with HindIII and Eco47III. Soybean thioredoxin is cloned by RT-PCR using total RNA from soybean germinated seeds and oligos P1 (5'-cgt agg atc cac cat ggc tga aga aga ggg tca ggt tgt c-3' (SEQ ID NO:31)) and P2 (5'-cgt aga gct ctc aag aag aag cag cag cag cag at-3' (SEQ ID NO:32)). This PCR product is cloned in pCR 2.1 TOPO vector and sequenced. This construct is used as the template in PCR with oligos P2 (5'-cgt aga gct ctc aag aag aag cag cag cag cag at-3' (SEQ ID NO:32)) and P5 (5'-gac tag cgc tga aga ggg tca ggt tgt cg-3' (SEQ ID NO:33)). Digest with Eco47III and SacI. 3-way ligation with the above three fragments, sequence is verified.

PNOV4102-β conglycinin α' subunit promoter-soybean thioredoxin-tobacco chitinase vacuolar signal sequence-NOS in PPO vector pNOV4100. Digest pNOV4100 with HindIII and SacI. Soybean—β conglycinin α' subunit promoter is cloned by PCR using soybean leaf genomic DNA and oligos P9 (5'-gac taa gct tac aat tat tat atc aaa atg gc-3' (SEQ ID NO:28)) and P10(5'-gct ttt ccc aat acg caa tgc-3' (SEQ ID NO:29)). This PCR product is cloned into pCR 2.1 TOPO vector and sequenced. This construct is used as template in PCR with oligos P4 (5'gac tag cgc tga cag aaa ctg atg cta gga a-3' (SEQ ID NO:30)) and P9 (5'-gac taa gct tac aat tat tat atc aaa atg gc-3' (SEQ ID NO:28)). Digest with HindIII and Eco47III. Soybean thioredoxin (Genbank accession # AI441505) is cloned by RT-PCR using total RNA from soybean germinated seeds and oligos P1 (5'-cgt agg atc cac cat ggc tga aga aga ggg tca ggt tgt c-3' (SEQ ID NO:31)) and P2 (5'-cgt aga gct ctc aag aag aag cag cag cag cag at-3' (SEQ ID NO:32)). This PCR product is cloned into pCR 2.1 TOPO vector and sequenced. This construct is used as the template in PCR with oligos P2 (5'-cgt aga gct ctc aag aag aag cag cag cag cag at-3' (SEQ ID NO:32)) and P5 (5'-gac tag cgc tga aga ggg tca ggt tgt cg-3' (SEQ ID NO:33)). Digest with Eco47III and SacI. 3-way ligation with the above three fragments, sequence is verified.

PNOV4103—β conglycinin α' subunit promoter plus propeptide portion of β conglycinin—soybean thioredoxin—NOS in PPO vector pNOV4100. Soybean β conglycinin α' subunit promoter plus propeptide portion of β conglycinin is cloned by PCR using soybean leaf genomic DNA and oligos P9 (5'-gac taa gct tac aat tat tat atc aaa atg gc-3' (SEQ ID NO:28)) and P12 (5'-cag tag gct taa gga ggt tgc aac gag-3' (SEQ ID NO:34)), this fragment is cloned into pCR 2.1 TOPO. This construct (12-4-4) is digested with StuI and SacI and soybean thioredoxin is cloned into this vector.

The restriction sites for soybean thioredoxin are modified by PCR. Oligos P2 (SacI) (5'-cgt aga gct ctc aag aag aag cag cag cag cag at-3' (SEQ ID NO:32)) and P11(PvuII) (5'-cag tca gct gaa gag ggt cag gtt gtc-3' (SEQ ID NO:35)). This yields β conglycinin promoter plus propeptide+thioredoxin in pCR 2.1 TOPO called A-6. A-6 and pNOV 4100 are digested with HindIII and SacI. The 1459bp fragment from A-6 is ligated to pNOV 4100.

PNOV4104—β conglycinin α' subunit promoter plus propeptide portion of β conglycinin-soybean thioredoxin-tobacco chitinase vacuolar signal sequence-NOS in PPO vector pNOV4100. Soybean β conglycinin promoter+propeptide in pCR 2.1 TOPO (12-4-4) digest with StuI and SacI. PCR fragment generated using P11 (5'-cag tca gct gaa gag ggt cag gtt gtc-3' (SEQ ID NO:35)) and P27 (5'-cta gga gct cta cat ggt gtc cac cag cag-3' (SEQ ID NO:36)), template BTC4 (pBluescript containing soybean thioredoxin and tobacco chitinase vacuolar signal sequence). Digest this fragment with PvuII and SacI, ligate with StuI-SacI fragment. This yields A3–10=pCR 2.1 TOPO with β conglycinin promoter+propeptide-soybean thioredoxin-tob. Chitinase vac. Signal sequence. Digest A3–10 and pNOV4100 with HindIII and SacI and ligate.

PNOV4105—Ubq3(At)-intron-tobacco chitinase ER signal sequence-NOS and PTX5'-AtPPO-35ST'. PNOV 4105=pNOV4100 digest with BamHI and PstI ligate to the tobacco chitinase ER signal sequence from pCIB 8418 digest with BamHI and PstI. This vector contains the Ubq3 promoter and intron with the tobacco chitinase ER signal sequence.

PNOV4106—Ubq3(At)-intron-tobacco chitinase ER signal sequence-soybean thioredoxin-tobacco chitinase vacuolar signal sequence-NOS in PPO vector pNOV4105. PNOV 4105 and pNov4102 are digested with Eco47III and SacI. The 387 bp band from pNOV4102 is ligated to digested pNOV4105.

PNOV4107—Ubq3(At)-intron-tobacco chitinase ER signal sequence-soybean thioredoxin-NOS in PPO vector pNOV4105. pNOV 4105 and pNOV4101 are digested with Eco47III and SacI. The 360 bp band from pNOV4101 is ligated to digested pNOV4105.

PNOV4108—β conglycinin α' subunit promoter-soybean thioredoxin-tobacco chitinase vacuolar signal sequence-NOS in binary vector pCIB200. Digest pCIB200 with XbaI and fill-in with Klenow. Digest pNOV4101 with HindIII and KpnI, make ends blunt with T4 DNA polymerase and ligate the 1626 bp band to digested pCIB200.

PNOV 4109—β conglycinin α' subunit promoter plus propeptide portion of β conglycinin—soybean thioredoxin—NOS in binary vector pCIB200. Digest pCIB200 with XbaI and fill-in with Klenow. Digest pNOV4103 with HindIII and KpnI, make ends blunt with T4 DNA polymerase and ligate the 1748 bp band to digested pCIB200.

PNOV4110—β conglycinin α' subunit promoter-soybean thioredoxin-NOS Digest pCIB200 with XbaI and fill-in with Klenow. Digest pNOV4102 with PvuII and KpnI, make ends blunt with T4 DNA polymerase and ligate the 1843 bp band to digested pCIB200.

PNOV4111—β conglycinin α' subunit promoter plus propeptide portion of β conglycinin-soybean thioredoxin-tobacco chitinase vacuolar signal sequence-NOS in binary vector pCIB200. Digest pCIB200 with XbaI and fill-in with Klenow. Digest pNOV4104 with PvuII and KpnI, make ends blunt with T4 DNA polymerase and ligate the 1969 bp band to digested pCIB200.

PNOV4112—Soybean thioredoxin in E. coli protein expression vector pET29a. Soybean thioredoxin is cloned by RT-PCR using total RNA from soybean germinated seeds and oligos P1 (5'-cgt agg atc cac cat ggc tga aga aga ggg tca ggt tgt c-3' (SEQ ID NO:31)) and P2 (5'-cgt aga gct ctc aag aag aag cag cag cag cag at-3' (SEQ ID NO:32)). This PCR product is digested with BamHI and SacI and cloned into pET29a digested with BamHI and SacI. The sequence is verified.

PNOV4113—Rice thioredoxin in E. coli protein expression vector pET29a. pNOV3400 is digested with BamHI and SacI, rice thioredoxin (378 bp) is cloned into pET29a which is digested with BamHI and SacI. The sequence is verified.

PNOV4114—Wheat thioredoxin in E. coli protein expression vector pET29a. pNOV3406 is digested with BamHI and SacI, wheat thioredoxin (387 bp) is cloned into pET29a which is digested with BamHI and SacI. The sequence is verified.

PNOV4115—Arabidopsis NADPH thioredoxin reductase in E. coli protein expression vector pET29a. Arabidopsis NADPH thioredoxin reductase (Genbank accession # Z23109) is cloned by RT-PCR. Total RNA is isolated from Arabidopsis leaf with Trizol (GibcoBRL, Gaithersburg, Md.) using the manufacturer's protocol. One microgram of total RNA is used in the Superscript one-step RT-PCR system (GibcoBRL, Gaithersburg, Md.) to generate cDNA and a PCR product in one step. Primers P28 (5'-gca cgg ctt ggt ggt gaa tcc-3' (SEQ ID NO:37)) and P29 (5'-ctc att ctg gtc cat caa tgt c-3' (SEQ ID NO:38)) are used in this reaction. The manufacturer's protocol is followed. The resulting PCR product is diluted 1:10 and 1 microliter is used in a nested PCR reaction with primers P26 (5'-gac tgt cga ctc aat cac tct tac ctt gct gag-3' (SEQ ID NO:39)) and P31 (5'-gac tgg atc caa tgg tct cga aac tca caa c-3' (SEQ ID NO:40)). The nested PCR product (998 bp) is gel purified, digested with BamHI and SalI and cloned into pET29a digested with BamHI and SalI. The sequence is verified. PNOV 4109-Digest pCIB200 with XbaI and fill-in with Klenow. Digest pNOV4103 with HindIII and KpnI, make ends blunt with T4 DNA polymerase and ligate the 1748 bp band to digested pCIB200. This construct is used for transient expression analysis in soybean as well as stable transformation of Arabidopsis and other dicots in conjuction with thioredoxin.

pNOV 4101, pNOV 4102, pNOV 4103, pNOV 4104, pNOV 4106, pNOV 4107 are used in transient expression experiments in soybean cotyledons.

Expression of thioredoxin is analyzed by western blot analysis.

PNOV 4108, PNOV 4109, PNOV 4110, PNOV 4111 are used in stable Arabidopsis transformation experiments. Expression of thioredoxin is analyzed by western blot analysis. The effect of thioredoxin on the expression and activity of seed specific proteins is tested.

PNOV 4112, 4113 and 4114 are constructs containing the soybean, rice and wheat trx-h genes, respectively, in an E. coli expression vector pET 29a (Novagen). These constructs are used to prepare thioredoxin protein for the production and purification of antibodies as well as standards in thioredoxin enzymatic assays.

Example 8

Protein Expression and Purification

The following constructs are used for protein expression in E. coli: pNOV4112 (soybean thioredoxin in pET29a), pNOV4113 (rice thioredoxin in pET29a), pNOV4114

(wheat thioredoxin in pET29a) and pNOV4115 (Arabidopsis thioredoxin reductase in pET29a). *E. coli* strain BL21(DE3) pLysS is transformed with each construct. A culture containing an aliquot from the glycerol stock, 50 micrograms/ml kanamycin, 34 micrograms/ml chloramphenicol in LB media is grown at 37° C. until the optical density measured at 600 nm reaches 0.6. The cultures are stored at 4° C. until the next day. These cultures are spun down and the cells resuspended in fresh LB. Large cultures are started using 1 ml of the small culture per 25 ml large culture. The cells are grown in LB with 50 micrograms/ml kanamycin, 34 micrograms/ml chloramphenicol at 37° C. until the optical density at 600 nm reached 0.6. IPTG (isopropyl-β-thiogalactopyranoside) is added to a final concentration of 0.4 mM to induce the expression of protein. The culture is grown for an additional 3 hours at 37° C. The culture is spun at 3000g for 10 minutes and the cells resuspended in BugBuster (Novagen, Madison, Wis.) using an amount equal to ⅕ of the culture volume. 5 units Dnase per ml BugBuster are added. The cells are placed at –20° C. over night. The cells are thawed and incubated with rotation at room temperature for 30 minutes. Cell debris is removed by centrifugation at 14,000g for 20 minutes at 4° C.

The expressed protein is a fusion protein containing the S-Tag (15 amino acids) and a thrombin cleavage site (6 amino acids) at the 5' end. Using the BamHI site as the 5' end cloning site of the cDNA, an additional 31 amino acids is added to the 5' end of the protein of interest.

The fusion protein is purified by affinity chromatography. Protein extract is added to S-protein Agarose slurry (Novagen, Madison, Wis.). The amount of S-protein agarose needed is determined for each experiment because the amount of fusion protein expressed varies. The yield is 0.5 mg purified protein/ml of resin. The manufacturer's protocol is followed.

To remove the S-Tag, the S-Tag Thrombin Purification kit (Novagen, Madison, Wis.) is used according to the manufacturer's protocol.

Example 9

Production of Antibodies

Soybean thioredoxin antibody production: Soybean thioredoxin is purified by affinity chromatography using S-protein agarose and the S-Tag is removed as described above. A contaminating protein is present in the preparation, therefore the protein is run on a 4–20% Tris-glycine gel (Novex, San Diego) and the soybean thioredoxin band cut from the gel. The gel slice is supplied to Duncroft, Inc. (Lovettsville, Va.) for antibody production in goat following standard operating procedure CG1 "Polyclonal Antibody Production in Rabbits, Sheep & Goats".

Rice Thioredoxin-Specific Antibody Purification: Rice thioredoxin is affinity purified with S-protein agarose (Novagen, Madison, Wis.) according to the manufacturer's protocol. The S-Tag is not removed.

Preparation of Affi-Gel-10 column: Purified rice thioredoxin (1 mg) is dialyzed against 2L of 0.1 M NaHCO$_3$ pH 8.3 for 5 hrs before coupling to Bio-rad Affi-Gel 10 gel according to the manufacturer's instructions. Briefly, approximately 2 ml of Affi-Gel 10 slurry is transferred to a glass fritted funnel that is attached to a vacuum, the solvent is removed, and the gel is washed twice with ice cold dH$_2$O (at least 3 bed volumes). The moist gel cake is then transferred to the tube containing the dialyzed rice thioredoxin and incubated at 4° C. overnight on a rotating wheel. To ensure that all unoccupied active sites are blocked, 0.1 ml of 1M ethanolamine HCL (pH 7.0) is added to the gel and rotated for 1 hr at 4° C. The gel is then transferred to a column, washed with PBS, pre-eluted with 0.1M glycine-HCl pH 2.5 (0.4 ml), and equilibrated in PBS. The final column volume is 0.8 ml. When not in use, the column is stored at 4° C. in PBS containing 0.2% sodium azide.

Purification of Rice Thioredoxin-Specific Antibodies: Soybean thioredoxin goat antiserum is immunoaffinity purified using an Affi-Gel 10 column of rice thioredoxin. For each run, 2 ml of serum is loaded by gravity onto the column. The column is washed with PBS until the A280 was <0.015, and then eluted with 0.4 ml 0.1M glycine-HCl pH 2.5. Fractions (1 ml) are collected and neutralized with 50 μl of 0.5M Tris pH 8.5. Fractions with an A$_{280}$ of 0.05 or greater are pooled.

Example 10

Thioredoxin Assays

Insulin reduction assay-(Arne Holmgren, (1979) *J.Biol.Chem.* 254: 9627–9632). In this assay DTT (dithiothreitol) reduces thioredoxin. Reduced thioredoxin then reduces the disulfide bonds in insulin causing a white precipitate to be formed. The rate of prcipitation is recorded at 650 nm. Freshly prepared solutions of insulin (1 mg/ml in 0.1M potassium phosphate pH 6.5), 2 mM EDTA (ethylenediaminetetraacetic acid), and 100 mM DTT are kept on ice. The assay mixture is prepared in cuvettes. Each cuvette contains 750 microliters 1mg/ml insulin, 3.3 microliters DTT, plus water to a final volume of 1 ml. The blank contains no thioredoxin, the samples contain various amounts of thioredoxin (minimum for assay is 10 micromolar). The samples are prepared and incubated for a minimum of 20 minutes at room temperature before reading the optical density at 650 nm.

DTNB[5,5'-dithiobis(2-nitrobenzoic acid)]assay-(Oblong et.al. (1993) Biochemistry 32: 7271–7277). In this assay, thioredoxin reductase and NADPH (nicotinamide adenine dinucleotide phosphate) are used to reduce thioredoxin which then reduces DTNB. The change in optical density at 412 nm is monitored over 4 minutes. Freshly prepared solutions of DTNB (100 mM in DMSO dimethyl sulfoxide), NADPH (20 mM in H$_2$O) and buffer 100 mM Tris pH 8.0, 0.1 mg/ml BSA are needed. The assay mixture is prepared in cuvettes. 10 microliters of DTNB, 10 microliters NADPH, 5 micrograms of thioredoxin, 2 micrograms of Arabidopsis or *E. coli* thioredoxin reductase and buffer to a final volume of 1 ml are added to the cuvette. As soon as the thioredoxin is added, mix by inversion and start measuring the change in optical density at 412 nm immediately. This is a slow reaction. The Y-axis should be set from 0 to 0.5A. The blank contains no thioredoxin.

Example 11

Agrobacterium-mediated Transformation of Maize

Transformation plasmids and selectable marker: The genes used for transformation are cloned into a vector suitable for maize transformation. Vectors used contain the phosphomannose isomerase (PMI) gene allowing for selection of transgenic cells with mannose.

Preparation of *Agrobacterium tumefaciens*: Agrobacterium strain LBA4404 (pSB1) containing the plant transformation plasmid is grown on YEPC (yeast extract (5 g/L), peptone 10 g/L), NaCl (5 g/L), CaCl$_2$2H$_2$O (1.029g/l)) solid medium with appropriate antibiotics (spectinomycin (100 mg/L), tetracycline (10 mg/L)) for 2–4 days at 28° C. Approximately 0.75×10$^8$ Agrobacterium are suspended in LS modified liquid infection media supplemented with 100 μM acetosyringone (Negrotto et al.,(2000) Plant Cell Rep in press: modified with 0.1× phosphate). Bacteria is pre-induced in this medium for 0.5–2 hrs before use. Bacteria concentration is checked at 660 nm and optical density is adjusted to approximately 0.75.

Inoculation: Immature embryos from A188, Hi-II or A188 ×Hi-II are excised from 8–9 day old ears directly into a 1.5 ml centrifuge tube containing LS modified liquid infection media supplemented with 100 μM acetosyringone. Total excision time is 30 minutes. Embryos are vortexed for 5 seconds, allowed to settle and infection medium is removed. Fresh infection medium is added. Embryos are heat shocked for 5 minutes at 45° C. by placing the tube in a water bath. Infection media is removed and replaced with Agrobacterium solution. Embryos are vortexed for 30 seconds and allowed to settle with the bacteria for 5 minutes. The bacteria/embryo solution is poured onto solidified LS modified infection media supplemented with 500 μM acetosyringone (Negrotto et al. ibid: modified with 0.1× phosphate). Bacteria solution is carefully pipetted off and embryos are moved to a clean section of the plate. Embryos are placed scutellum side up and are co-cultured for 2–3 days at 22° C.

Selection of transformed cells and regeneration of transformed plants: Following co-culture, embryos are placed on JMS media (Suttie et al., (1991) 3$^{rd}$ International Congress Molecular Biology of Plant Growth and Development Poster #905) supplemented with AgNO$_3$ and 200 mg/L ticarcillin for callus initiation. Ticarcillin is used in all subsequent media. After 10 days of culture in the dark at 28° C. embryogenic callus has initiated. Callus is transferred to JMS medium without silver and with 10 g/L mannose, 5 g/L sucrose for selection. After 2–3 weeks, surviving callus is transferred to fresh selection media. Following 2–3 weeks, surviving callus is transferred to MSAK+PO$_4$ medium (Murashige and Skoog (1962) Physiol. Plant. 15:473–439: supplemented with 20 g/L sucrose, 5 g/L mannose, ancimidol (0.25 mg/L), kinetin (0.5 mg/L) and KH$_2$PO$_4$ (170 mg/L)) for regeneration (28° C., dark, 10–14 days). Callus is transferred to fresh MSAK+PO$_4$ media and transferred to the light (16 hr light/8 hr dark). After 1 week, regenerating shoots are transferred to MS media without hormones supplemented with 20 g/L sucrose and 5 g/L mannose. Rooted shoots are transferred to Magenta™ GA-7 boxes with 0.75 strength MS media supplemented with 10 ml/L of Plant Preservative Mixture™ and 10 g/L sucrose for further growth. Analysis is performed on plants directly from GA-7 boxes or plants transferred to soil.

Example 12

Soybean Cotyledon Transient Expression System

Sterilized seeds of the S3911 Novartis breeding line are germinated, 5/plate, on MS solid medium for 6 days under 16/8 photoperiod, 25° C. The cotyledons are explanted and sliced into 1–2 mm cubes. The cubes form a pair of cotyledons are arranged in a circle, 1–2 cm in diameter, in the center of a petri plate containing MS medium with 1 mg/1 BAP and 0.5 mg/L NAA. The tissue is bombarded with the PDS-1000 Helium gun according to the DuPont manual. Each plate is shot 2 times using 1550 psi rupture disks. The gold microcarriers with DNA are prepared according to the manual. 0.6 μg of selected plasmid DNA are applied to each macrocarrier. A stainless steel screen is used to baffle the shock wave. After bombardment, the plates are returned to 16/8 photoperiod, 25° C. The first sampling is at 48 hours.

Example 13

Analysis of Transgenic Plants Transformed with pNOV 3401 A. PCR

Samples are taken from transgenic plants in the GA-7 boxes. DNA is extracted as per manufacturer's directions using a Gentra DNA extraction kit in a 96 well format. PCR is done using Jumpstart Redtaq Readymix (Sigma) and primers Thiorodoxubi 1603 (5'-GCGGTCGTTC ATTCGTTCTA-3' (SEQ ID NO:41)) and Thiorodox 2364 (5'-ACGTGCTTCA CGATGGTGTT-3' (SEQ ID NO:42)), at final concentration of 2.5 μM each. Transgenic plants identified by PCR to contain the thioredoxin gene are transferred to the greenhouse.

B. Analysis of thioredoxin RNA from transgenic plants by Northern Blot analysis:

Total RNA is prepared from leaf and seed tissue of transgenic plants by the method described in Lagrimini et al. ((1987) Proc. Natl. Acad. Sci, 84: 7542–7546). The probe is prepared from the complete rice trx-h gene. Plasmid pNOV 3401 is digested with BamHI-SacI to obtain a 327 bp fragment which is gel purified and labelled with $^{32}$p α-CTP using the random primer labelling kit from Life Technologies Inc.

Northern blot analysis of leaf and seed RNA from representative transgenic plants shows expression of the thioredoxin mRNA in leaf and seed tissue.

C. Analysis of thioredoxin proteins from transgenic plants:

Protein extraction and western analysis of corn leaf samples: A small circle, the size of the eppendorf lid, is punched from each leaf sample. The tissue is placed in an eppendorf tube and frozen in dry ice. A small pestle is used to grind the tissue in the eppendorf. 400 microliters of 100 mM Tris pH 8.0 is added to the ground tissue, the samples are rotated at room temperature for thirty minutes, spun down and the extract saved. All samples are concentrated using centricons with 3000 MW cutoff. 12.5 microliters of each sample is run on a 16% Tris-glycine (Novex, San Diego Calif.) mini gel with tris-glycine-SDS (24 mM Tris 52 mM glycine 1% sodium dodecyl sulfate) running buffer, the protein is transferred to PVDF. The blot is blocked in TBS-2% Tween (TBS-150 mM NaCl 30 mM Tris pH 10.2) for 15 minutes at room temperature, incubated with rice thioredoxin antibody (affinity purified from goat anti-soybean thioredoxin) 1 microgram antibody per 1 milliliter TBS-0.05% tween at 4 degrees C overnight. The blot is washed with TBS-0.05% tween 3 times for 5 minutes, incubated with HRP (horse radish peroxidase) rabbit anti-goat IgG (50 nanograms antibody per millilter TBS-0.05% tween for 1 hour at room temperature, washed with TBS-0.05% tween, incubated with supersignal west femto chemi-luminescent substrate (Pierce, Rockford, Ill.) for 5 minutes at room temperature. The blot is placed against film and exposed for 30 seconds.

Protein extraction and western analysis of corn seed samples: One seed from each is cut in half, one half is frozen in dry ice and ground by mortar and pestle, 1.5 milliliters Tris pH 8.0 is added to each and incubated with rotation at room temperature for 30 minutes. The samples are spun and the protein extract from each is concentrated using centricons with a 10,000 MW cut off. 12.5 microliters of each sample is run on a 16% tris-glycine gel (same conditions as leaf samples). The gel is transferred to nitrocellulose, blocked with TBS-2% tween for 15 minutes, incubated with rice thioredoxin antibody (1 microgram antibody per 1 milliliter TBS-0.05% tween) for 1.5 hours at room temperature, washed and incubated with HRP rabbit anti-goat IgG as described above. The blot is incubated with supersignal west pico chemiluminescent substrate (Pierce, Rockford, Ill.) for 5 minutes at room temperature. The blot is placed against film and exposed for 5 minutes. Western blot analysis shows expression of the rice thioredoxin protein in leaf and seed tissue. The Western blot analysis also shows that the rice thioredoxin expressed in transgenic plants has the expected size when compared to a control rice thioredoxin loaded on the same gel.

EXAMPLE 14

Enzymatic Activity of Recombinant Thioredoxin and Thioredoxin Reductase Expressed in *E. coli*

Recombinant soybean thioredoxin expressed in *E. coli* is purified by affinity chromatography with S-protein agarose and the S-Tag removed by thrombin cleavage. This protein is tested in the insulin reduction assay as described. 4, 20, 40 and 80 micrograms of affinity purified thioredoxin (one contaminating protein present) is tested. After 31 minutes, a change in optical density at 650 nm is measured.

| Thioredoxin ($\mu g$) | OD 650 nm (after 31 minutes) | Rate of Precipitation ($\Delta A_{650}$/min) |
|---|---|---|
| 0 | .0000 | .000000 |
| 4 | .0010 | .000032 |

| Thioredoxin ($\mu g$) | OD 650 nm (after 31 minutes) | Rate of Precipitation ($\Delta A_{650}$/min) |
|---|---|---|
| 5 | .0077 | .00025 |
| 6 | .0084 | .00027 |
| 7 | .0117 | .00038 |

The following recombinant proteins are tested in the NADPH thioredoxin reductase DTNB assay: soybean thioredoxin with S-tag, soybean thioredoxin prep without S-tag, rice thioredoxin with S-tag, wheat thioredoxin with S-tag and Arabidopsis thioredoxin reductase without S-tag. *E. coli* thioredoxin reductase (T-7915, Sigma, St. Louis, Mo.) is also used in the assays. The change in optical density at 412 nm is monitored over 4 min.

| Thioredoxin | Thioredoxin Reductase | $\Delta A_{412}$ |
|---|---|---|
| 0 $\mu l$ | 1.5 $\mu l$ (≈0.5 $\mu g$) Arabidopsis | 0.06 |
| 30 $\mu l$ (≈12 $\mu g$) soybean | 2.3 $\mu g$ *E.coli* | 0.333 |
| 30 $\mu l$ (≈12 $\mu g$) soybean | 1.5 $\mu l$ (≈0.5 $\mu g$) Arabidopsis | 0.42 |
| 30 $\mu l$ (≈6 $\mu g$) soybean | 2.3 $\mu g$ *E.coli* | 0.20 |
| 30 $\mu l$ (≈15 $\mu g$) rice | 1.5 $\mu l$ (≈0.5 $\mu g$) Arabidopsis | 0.66 |
| 30 $\mu l$ (≈15 $\mu g$) rice | 2.3 $\mu g$ *E.coli* | 0.30 |
| 30 $\mu l$ (≈0.6 $\mu g$) wheat | 2.3 $\mu g$ *E.coli* | 0.30 |
| 30 $\mu l$ (≈0.6 $\mu g$) wheat | 1.5 $\mu l$ (≈0.5 $\mu g$) Arabidopsis | 0.08 |
| 30 $\mu l$ (≈1.2 $\mu g$) wheat | 1.5 $\mu l$ (≈0.5 $\mu g$) Arabidopsis | 0.08 |

Arabidopsis thioredoxin reductase and *E. coli* thioredoxin reductase can reduce soybean thioredoxin with and without the S-tag. Arabidopsis and *E. coli* thioredoxin reductases can also reduce rice thioredoxin. Wheat thioredoxin can be reduced by *E. coli* thioredoxin reductase but not by Arabidopsis thioredoxin reductase.

What is claimed is:

1. An isolated nucleic acid molecule comprising SEQ ID NO:24.

2. A chimeric gene comprising a promoter active in plants operatively linked to the nucleic acid molecule of claim 1.

3. A recombinant vector comprising the chimeric gene of claim 2.

4. A transgenic host cell comprising the chimeric gene of claim 2.

5. A transgenic host cell according to claim 4, which is a transgenic plant cell.

6. A transgenic plant comprising the transgenic plant cell of claim 5.

7. The transgenic plant of claim 6, which is corn or soybean.

8. Seed from a transgenic plant according to claim 6, wherein said seed comprises the chimeric gene.

* * * * *

SEQUENCE LISTING

<160> NUMBER OF SEQ ID NOS: 42

<210> SEQ ID NO 1
<211> LENGTH: 85
<212> TYPE: PRT
<213> ORGANISM: Methanococcus jannaschii

<400> SEQUENCE: 1

Met Ser Lys Val Lys Ile Glu Leu Phe Thr Ser Pro Met Cys Pro His
1               5                   10                  15

Cys Pro Ala Ala Lys Arg Val Val Glu Glu Val Ala Asn Glu Met Pro
            20                  25                  30

Asp Ala Val Glu Val Glu Tyr Ile Asn Val Met Glu Asn Pro Gln Lys
        35                  40                  45

Ala Met Glu Tyr Gly Ile Met Ala Val Pro Thr Ile Val Ile Asn Gly
    50                  55                  60

Asp Val Glu Phe Ile Gly Ala Pro Thr Lys Glu Ala Leu Val Glu Ala
65                  70                  75                  80

Ile Lys Lys Arg Leu
                85

-continued

```
<210> SEQ ID NO 2
<211> LENGTH: 119
<212> TYPE: PRT
<213> ORGANISM: Archaeoglobus fulgidus

<400> SEQUENCE: 2

Met Pro Met Val Arg Lys Ala Ala Phe Tyr Ala Ile Ala Val Ile Ser
 1               5                  10                  15

Gly Val Leu Ala Ala Val Val Gly Asn Ala Leu Tyr His Asn Phe Asn
             20                  25                  30

Ser Asp Leu Gly Ala Gln Ala Lys Ile Tyr Phe Phe Tyr Ser Asp Ser
         35                  40                  45

Cys Pro His Cys Arg Glu Val Lys Pro Tyr Val Glu Glu Phe Ala Lys
     50                  55                  60

Thr His Asn Leu Thr Trp Cys Asn Val Ala Glu Met Asp Ala Asn Cys
 65                  70                  75                  80

Ser Lys Ile Ala Gln Glu Phe Gly Ile Lys Tyr Val Pro Thr Leu Val
                 85                  90                  95

Ile Met Asp Glu Glu Ala His Val Phe Val Gly Ser Asp Glu Val Arg
            100                 105                 110

Thr Ala Ile Glu Gly Met Lys
        115

<210> SEQ ID NO 3
<211> LENGTH: 93
<212> TYPE: PRT
<213> ORGANISM: Archaeoglobus fulgidus

<400> SEQUENCE: 3

Met Val Phe Thr Ser Lys Tyr Cys Pro Tyr Cys Arg Ala Phe Glu Lys
 1               5                  10                  15

Val Val Glu Arg Leu Met Gly Glu Leu Asn Gly Thr Val Glu Phe Glu
             20                  25                  30

Val Val Asp Val Asp Glu Lys Arg Glu Leu Ala Glu Lys Tyr Glu Val
         35                  40                  45

Leu Met Leu Pro Thr Leu Val Leu Ala Asp Gly Asp Glu Val Leu Gly
     50                  55                  60

Gly Phe Met Gly Phe Ala Asp Tyr Lys Thr Ala Arg Glu Ala Ile Leu
 65                  70                  75                  80

Glu Gln Ile Ser Ala Phe Leu Lys Pro Asp Tyr Lys Asn
                 85                  90

<210> SEQ ID NO 4
<211> LENGTH: 134
<212> TYPE: PRT
<213> ORGANISM: Archaeoglobus fulgidus

<400> SEQUENCE: 4

Met Asp Glu Leu Glu Leu Ile Arg Gln Lys Lys Leu Lys Glu Met Met
 1               5                  10                  15

Gln Lys Met Ser Gly Glu Lys Ala Arg Lys Val Leu Asp Ser Pro
             20                  25                  30

Val Lys Leu Asn Ser Ser Asn Phe Asp Glu Thr Leu Lys Asn Asn Glu
         35                  40                  45

Asn Val Val Val Asp Phe Trp Ala Glu Trp Cys Met Pro Cys Lys Met
     50                  55                  60

Ile Ala Pro Val Ile Glu Glu Leu Ala Lys Glu Tyr Ala Gly Lys Val
 65                  70                  75                  80
```

```
Val Phe Gly Lys Leu Asn Thr Asp Glu Asn Pro Thr Ile Ala Ala Arg
                85                  90                  95

Tyr Gly Ile Ser Ala Ile Pro Thr Leu Ile Phe Phe Lys Lys Gly Lys
            100                 105                 110

Pro Val Asp Gln Leu Val Gly Ala Met Pro Lys Ser Glu Leu Lys Arg
        115                 120                 125

Trp Val Gln Arg Asn Leu
    130
```

<210> SEQ ID NO 5
<211> LENGTH: 105
<212> TYPE: PRT
<213> ORGANISM: Archaeoglobus fulgidus

<400> SEQUENCE: 5

```
Met Glu Arg Leu Asn Ser Glu Arg Phe Arg Glu Val Ile Gln Ser Asp
  1               5                  10                  15

Lys Leu Val Val Asp Phe Tyr Ala Asp Trp Cys Met Pro Cys Arg
                20                  25                  30

Tyr Ile Ser Pro Ile Leu Glu Lys Leu Ser Lys Glu Tyr Asn Gly Glu
            35                  40                  45

Val Glu Phe Tyr Lys Leu Asn Val Asp Glu Asn Gln Asp Val Ala Phe
    50                  55                  60

Glu Tyr Gly Ile Ala Ser Ile Pro Thr Val Leu Phe Phe Arg Asn Gly
 65                  70                  75                  80

Lys Val Val Gly Gly Phe Ile Gly Ala Met Pro Glu Ser Ala Val Arg
                85                  90                  95

Ala Glu Ile Glu Lys Ala Leu Gly Ala
            100                 105
```

<210> SEQ ID NO 6
<211> LENGTH: 301
<212> TYPE: PRT
<213> ORGANISM: Methanococcus jannaschii

<400> SEQUENCE: 6

```
Met Ile His Asp Thr Ile Ile Gly Ala Gly Pro Gly Gly Leu Thr
  1               5                  10                  15

Ala Gly Ile Tyr Ala Met Arg Gly Lys Leu Asn Ala Leu Cys Ile Glu
                20                  25                  30

Lys Glu Asn Ala Gly Gly Arg Ile Ala Glu Ala Gly Ile Val Glu Asn
            35                  40                  45

Tyr Pro Gly Phe Glu Glu Ile Arg Gly Tyr Glu Leu Ala Glu Lys Phe
    50                  55                  60

Lys Asn His Ala Glu Lys Phe Lys Leu Pro Ile Ile Tyr Asp Glu Val
 65                  70                  75                  80

Ile Lys Ile Glu Thr Lys Glu Arg Pro Phe Lys Val Ile Thr Lys Asn
                85                  90                  95

Ser Glu Tyr Leu Thr Lys Thr Ile Val Ile Ala Thr Gly Thr Lys Pro
            100                 105                 110

Lys Lys Leu Gly Leu Asn Glu Asp Lys Phe Ile Gly Arg Gly Ile Ser
        115                 120                 125

Tyr Cys Thr Met Cys Asp Ala Phe Phe Tyr Leu Asn Lys Glu Val Ile
    130                 135                 140

Val Ile Gly Arg Asp Thr Pro Ala Ile Met Ser Ala Ile Asn Leu Lys
145                 150                 155                 160
```

```
Asp Ile Ala Lys Lys Val Ile Val Ile Thr Asp Lys Ser Glu Leu Lys
                165                 170                 175

Ala Ala Glu Ser Ile Met Leu Asp Lys Leu Lys Glu Ala Asn Asn Val
            180                 185                 190

Glu Ile Ile Tyr Asn Ala Lys Pro Leu Glu Ile Val Gly Glu Glu Arg
        195                 200                 205

Ala Glu Gly Val Lys Ile Ser Val Asn Gly Lys Glu Glu Ile Ile Lys
    210                 215                 220

Ala Asp Gly Ile Phe Ile Ser Leu Gly His Val Pro Asn Thr Glu Phe
225                 230                 235                 240

Leu Lys Asp Ser Gly Ile Glu Leu Asp Lys Lys Gly Phe Ile Lys Thr
                245                 250                 255

Asp Glu Asn Cys Arg Thr Asn Ile Asp Gly Ile Tyr Ala Val Gly Asp
            260                 265                 270

Val Arg Gly Gly Val Met Gln Val Ala Lys Ala Val Gly Asp Gly Cys
        275                 280                 285

Val Ala Met Ala Asn Ile Ile Lys Tyr Leu Gln Lys Leu
    290                 295                 300

<210> SEQ ID NO 7
<211> LENGTH: 300
<212> TYPE: PRT
<213> ORGANISM: Archaeoglobus fulgidus

<400> SEQUENCE: 7

Met Tyr Asp Val Ala Ile Ile Gly Gly Pro Ala Gly Leu Thr Ala
1               5                   10                  15

Ala Leu Tyr Ser Ala Arg Tyr Gly Leu Lys Thr Val Phe Glu Thr
            20                  25                  30

Val Asp Pro Val Ser Gln Leu Ser Leu Ala Ala Lys Ile Glu Asn Tyr
        35                  40                  45

Pro Gly Phe Glu Gly Ser Gly Met Glu Leu Leu Glu Lys Met Lys Glu
    50                  55                  60

Gln Ala Val Lys Ala Gly Ala Glu Trp Lys Leu Glu Lys Val Glu Arg
65                  70                  75                  80

Val Glu Arg Asn Gly Glu Thr Phe Thr Val Ile Ala Glu Gly Gly Glu
                85                  90                  95

Tyr Glu Ala Lys Ala Ile Ile Val Ala Thr Gly Gly Lys His Lys Glu
            100                 105                 110

Ala Gly Ile Glu Gly Glu Ser Ala Phe Ile Gly Arg Gly Val Ser Tyr
        115                 120                 125

Cys Ala Thr Cys Asp Gly Asn Phe Phe Arg Gly Lys Lys Val Ile Val
130                 135                 140

Tyr Gly Ser Gly Lys Glu Ala Ile Glu Asp Ala Ile Tyr Leu His Asp
145                 150                 155                 160

Ile Gly Cys Glu Val Thr Ile Val Ser Arg Thr Pro Ser Phe Arg Ala
                165                 170                 175

Glu Lys Ala Leu Val Glu Val Glu Lys Arg Gly Ile Pro Val His
            180                 185                 190

Tyr Ser Thr Thr Ile Arg Lys Ile Ile Gly Ser Gly Lys Val Glu Lys
        195                 200                 205

Val Val Ala Tyr Asn Arg Glu Lys Lys Glu Glu Phe Glu Ile Glu Ala
    210                 215                 220

Asp Gly Ile Phe Val Ala Ile Gly Met Arg Pro Ala Thr Asp Val Val
```

```
225                 230                 235                 240
Ala Glu Leu Gly Val Glu Arg Asp Ser Met Gly Tyr Ile Lys Val Asp
                245                 250                 255
Lys Glu Gln Arg Thr Asn Val Glu Gly Val Phe Ala Ala Gly Asp Cys
            260                 265                 270
Cys Asp Asn Pro Leu Lys Gln Val Val Thr Ala Cys Gly Asp Gly Ala
        275                 280                 285
Val Ala Ala Tyr Ser Ala Tyr Lys Tyr Leu Thr Ser
    290                 295                 300

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:
      oligonucleotide (primer NMD109)

<400> SEQUENCE: 8
ggatccacca tggccgccga ggag                                          24

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:
      oligonucleotide (primer NMD110)

<400> SEQUENCE: 9
gagctcttag gcagaagcag atg                                           23

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:
      oligonucleotide (primer NMD 102)

<400> SEQUENCE: 10
ggatccacca tggcggcgtc gg                                            22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:
      oligonucleotide (primer NMD103)

<400> SEQUENCE: 11
gagctcttac tgggccgcgt gt                                            22

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence:
      oligonucleotide (primer NMD124A)

<400> SEQUENCE: 12
gagctcttag gcgctagcag atg                                           23
```

```
<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:
      oligonucleotide (primer NMD125A)

<400> SEQUENCE: 13
ggatccacca gcgctgccga                                              20

<210> SEQ ID NO 14
<211> LENGTH: 65
<212> TYPE: DNA
<213> ORGANISM: Artificial Sequence
<220> FEATURE:
<223> OTHER INFORMATION: Description of Artificial Sequence:
      oligonucleotide (primer NMD126)

<400> SEQUENCE: 14
gatccaccat gagggtgttg ctcgttgccc tcgctctcct ggctctcgct gcgagcgcca   60
ccagc                                                              65

<210> SEQ ID NO 15
<211> LENGTH: 61
<212> TYPE: DNA
<213> ORGANISM: Artificial Sequence
<220> FEATURE:
<223> OTHER INFORMATION: Description of Artificial Sequence:
      oligonucleotide (primer NMD 127)

<400> SEQUENCE: 15
gctggtggcg ctcgcagcga gagccaggag agcgagggca acgagcaaca ccctcatggt   60
g                                                                  61

<210> SEQ ID NO 16
<211> LENGTH: 67
<212> TYPE: DNA
<213> ORGANISM: Artificial Sequence
<220> FEATURE:
<223> OTHER INFORMATION: Description of Artificial Sequence:
      oligonucleotide (primer NMD 128)

<400> SEQUENCE: 16
ctagcgctct gcagcagccg actccatgcc cctacgctgc tgccggcggt gtcccccact   60
gagagct                                                            67

<210> SEQ ID NO 17
<211> LENGTH: 59
<212> TYPE: DNA
<213> ORGANISM: Artificial Sequence
<220> FEATURE:
<223> OTHER INFORMATION: Description of Artificial Sequence:
      oligonucleotide (primer NMD129)

<400> SEQUENCE: 17
ctcagtgggg gacaccgccg gcagcagcgt aggggcatgg agtcggctgc tgcagagcg    59

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:
      oligonucleotide (primer STRF1A)
```

<400> SEQUENCE: 18
ggatccacca tgaacggcct ggag                                              24

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence:
      oligonucleotide (primer STRF1B)

<400> SEQUENCE: 19
ctcgagaagt ccaccttggt cac                                               23

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence:
      oligonucleotide (primer STRF2A)

<400> SEQUENCE: 20
ctcgagcaag ccgttcaa                                                     18

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence:
      oligonucleotide (primer STRF2B)

<400> SEQUENCE: 21
gacgtcgatc ttcgggttgg a                                                 21

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:
      oligonucleotide (primer STR3A)

<400> SEQUENCE: 22
cgacgtcatc tggaactcct                                                   20

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence:
      oligonucleotide (primer STR3B)

<400> SEQUENCE: 23
gagctcagat ctagtcggac ttg                                               23

<210> SEQ ID NO 24
<211> LENGTH: 1021
<212> TYPE: DNA
<213> ORGANISM: Arabidopsis thaliana

<400> SEQUENCE: 24
ggatccacca tgaacggcct ggagactcac aacacccgcc tctgcatcgt tggctccggc       60

-continued

```
ccggctgccc acaccgccgc catctacgcc gcccgcgccg agctgaagcc gctcctcttc    120
gagggctgga tggccaacga catcgccccg ggcggccagc tcaccaccac caccgacgtg    180
gagaacttcc ccggcttccc ggagggcatc ctcggcgtgg agctgaccga caagttccgc    240
aagcagagcg agcgcttcgg caccaccatc ttcaccgaga ccgtgaccaa ggtggacttc    300
tcgagcaagc cgttcaagct cttcaccgac tccaaggcca tcctcgccga cgccgtgatc    360
ctcgccatcg gcgccgtggc caagtggctc tccttcgtgg gctccggcga ggtgctcggc    420
ggcctctgga accgcggcat ctccgcctgc gctgtgtgcg acggcgccgc ccgatcttc    480 cgcaacaagc cgctcgctgt gatcggtggc ggagacagcg cgatggagga ggccaacttc    540
ctcaccaagt acggctccaa ggtgtacatc atcgaccgcc gcgacgcctt ccgcgcctcc    600
aagatcatgc agcagcgcgc cctctccaac ccgaagatcg acgtcatctg aactcctcc     660 gtggtggagg cctacggcga cggcgagcgc gacgtgctcg gcggcctcaa ggtgaagaac    720
gtggtgaccg gcgacgtgtc cgacctcaag gtgtccggcc tcttcttcgc catcggccac    780
gagccggcca ccaagttcct cgacggcggc gtggagctgg actccgacgg ctacgtggtg    840
accaagccgg gcaccaccca gacctccgtg cctggcgtgt cgccgccgg cgacgtgcag    900 gacaagaagt accgccaggc catcaccgcc gccggcaccg gctgcatggc cgccctcgac    960
gccgagcact acctccagga gatcggctcc cagcagggca gtccgactaa gatctgagct   1020
c                                                                   1021
```

<210> SEQ ID NO 25
<211> LENGTH: 333
<212> TYPE: PRT
<213> ORGANISM: Arabidopsis thaliana

<400> SEQUENCE: 25

```
Met Asn Gly Leu Glu Thr His Asn Thr Arg Leu Cys Ile Val Gly Ser
  1               5                  10                  15

Gly Pro Ala Ala His Thr Ala Ala Ile Tyr Ala Ala Arg Ala Glu Leu
             20                  25                  30

Lys Pro Leu Leu Phe Glu Gly Trp Met Ala Asn Asp Ile Ala Pro Gly
         35                  40                  45

Gly Gln Leu Thr Thr Thr Thr Asp Val Glu Asn Phe Pro Gly Phe Pro
     50                  55                  60

Glu Gly Ile Leu Gly Val Glu Leu Thr Asp Lys Phe Arg Lys Gln Ser
 65                  70                  75                  80

Glu Arg Phe Gly Thr Thr Ile Phe Thr Glu Thr Val Thr Lys Val Asp
                 85                  90                  95

Phe Ser Ser Lys Pro Phe Lys Leu Phe Thr Asp Ser Lys Ala Ile Leu
            100                 105                 110

Ala Asp Ala Val Ile Leu Ala Ile Gly Ala Val Ala Lys Trp Leu Ser
        115                 120                 125

Phe Val Gly Ser Gly Glu Val Leu Gly Gly Leu Trp Asn Arg Gly Ile
    130                 135                 140

Ser Ala Cys Ala Val Cys Asp Gly Ala Ala Pro Ile Phe Arg Asn Lys
145                 150                 155                 160

Pro Leu Ala Val Ile Gly Gly Gly Asp Ser Ala Met Glu Glu Ala Asn
                165                 170                 175

Phe Leu Thr Lys Tyr Gly Ser Lys Val Tyr Ile Ile Asp Arg Arg Asp
            180                 185                 190
```

```
Ala Phe Arg Ala Ser Lys Ile Met Gln Gln Arg Ala Leu Ser Asn Pro
            195                 200                 205
Lys Ile Asp Val Ile Trp Asn Ser Ser Val Val Glu Ala Tyr Gly Asp
210                 215                 220
Gly Glu Arg Asp Val Leu Gly Leu Lys Val Lys Asn Val Val Thr
225                 230                 235                 240
Gly Asp Val Ser Asp Leu Lys Val Ser Gly Leu Phe Phe Ala Ile Gly
                245                 250                 255
His Glu Pro Ala Thr Lys Phe Leu Asp Gly Val Glu Leu Asp Ser
            260                 265                 270
Asp Gly Tyr Val Val Thr Lys Pro Gly Thr Thr Gln Thr Ser Val Pro
            275                 280                 285
Gly Val Phe Ala Ala Gly Asp Val Gln Asp Lys Lys Tyr Arg Gln Ala
            290                 295                 300
Ile Thr Ala Ala Gly Thr Gly Cys Met Ala Ala Leu Asp Ala Glu His
305                 310                 315                 320
Tyr Leu Gln Glu Ile Gly Ser Gln Gln Gly Lys Ser Asp
                325                 330

<210> SEQ ID NO 26
<211> LENGTH: 1560
<212> TYPE: DNA
<213> ORGANISM: Oryza sativa

<400> SEQUENCE: 26
aytcagatat gttatccaga ttctaaatgt gctataggg wtaaatgtgt gttcatatgg      60
gagatatatc agtttcagtt tttttggaag gtgtttatag gagttmggcg cgttttaaar   120
ktgtggtatg catcgtgttg tgarttgttk gtgtgttycy ttaaaaaaaa awttgccatt   180
tgtcaattat tgtggaattt ctgcaacttg ttgtccmaag kaaaaggaaa atagtttcgg   240
tcaacaactc aacatccatc tgggggtatg accgaccgag cgcggtggcc gttgattggc   300
tcgtcgcctc ctcccttctc ggtctgacgt tctgaccagt gccgggtagg aagcgtaatt   360
ttgaggagag actccgaccc cgccgccgc cgccgcagcc aagccatgga gggatccgcc   420
ggggcgccgc tccgcacgcg cctgtgcatc atcgggagcg gccgtcggc gcacacggcg   480
gcgatctacg ccgccgcgc ggagctcaag cccgtgctct cgagggctg gctcgccaac   540
gacatcgcgg cgggggccca gctcaccacc accaccgacg tcgagaactt cccgggttc   600
cccgagggga tcctcggcgg cgagctcatg gatcggtgcc gcgcccagtc cctccggttc   660
ggcaccagca tcatctccga gaccgtcacc gcggtcgact ctccgcccg cccttccgc     720
gtcgcctccg actccaccac cgtgctcgcc gacgccgtcg tcgtcgccac cggcgccgtc   780
gcccggcgac tccacttcgc cggctccgac gcctactgga accgcggcat ctcagcctgc   840
gccgtctgcg acgggccgc cccaatcttc aggaacaaac ccatcgccgt catcggcggc   900
ggcgactccg ccatggagga gtccaacttc ctcaccaagt acggctccca tgtgtacatc   960
atccaccgcc gcaacacctt ccgcgcctcc aagatcatgc aggccagggc gttgtcaaac  1020
cccaagatcc aggttttctg ggactctgag gtcgtcgagg cctacggcgg cgagggtgga  1080
ggtccattgg ctggtgtcaa ggtgaagaac ttggttactg ggaagatctc cgaccttcag  1140
gtgtccggtc tcttcttcgc catcggacat gaaccggcga cgaagtttct cggcgggcag  1200
cttgagctcg atgctgatgg gtatgtggcc accaagccag gctccacgca caccagtgtg  1260
aagggggtct tgctgctgg ggatgtgcag gacaagaagt atcgccaggc tattactgcc  1320
```

```
gctggatcag gtttgtgaat tgatgatttt tcaggttacc tgtgattaat ttttttctgc    1380
actttcttag agatcagtcg cttcatgggt tgctatttgc tagtgcgaat tgcaatagaa    1440
attgttcagg gcttgagtat gtagtgagcg aatgatgatg gtcaaaatta gaaccttttt    1500
aagctatcat agagttaacg tgtttgagtt tctgaaataa gtgctttcat tatgtatcta    1560
```

<210> SEQ ID NO 27
<211> LENGTH: 310
<212> TYPE: PRT
<213> ORGANISM: Oryza sativa

<400> SEQUENCE: 27

```
Met Glu Gly Ser Ala Gly Ala Pro Leu Arg Thr Arg Leu Cys Ile Ile
  1               5                  10                  15

Gly Ser Gly Pro Ser Ala His Thr Ala Ala Ile Tyr Ala Ala Arg Ala
             20                  25                  30

Glu Leu Lys Pro Val Leu Phe Glu Gly Trp Leu Ala Asn Asp Ile Ala
         35                  40                  45

Ala Gly Gly Gln Leu Thr Thr Thr Thr Asp Val Glu Asn Phe Pro Gly
     50                  55                  60

Phe Pro Glu Gly Ile Leu Gly Glu Leu Met Asp Arg Cys Arg Ala
 65                  70                  75                  80

Gln Ser Leu Arg Phe Gly Thr Ser Ile Ile Ser Glu Thr Val Thr Ala
                 85                  90                  95

Val Asp Phe Ser Ala Arg Pro Phe Arg Val Ala Ser Asp Ser Thr Thr
            100                 105                 110

Val Leu Ala Asp Ala Val Val Val Ala Thr Gly Ala Val Ala Arg Arg
        115                 120                 125

Leu His Phe Ala Gly Ser Asp Ala Tyr Trp Asn Arg Gly Ile Ser Ala
    130                 135                 140

Cys Ala Val Cys Asp Gly Ala Ala Pro Ile Phe Arg Asn Lys Pro Ile
145                 150                 155                 160

Ala Val Ile Gly Gly Gly Asp Ser Ala Met Glu Glu Ser Asn Phe Leu
                165                 170                 175

Thr Lys Tyr Gly Ser His Val Tyr Ile Ile His Arg Arg Asn Thr Phe
            180                 185                 190

Arg Ala Ser Lys Ile Met Gln Ala Arg Ala Leu Ser Asn Pro Lys Ile
        195                 200                 205

Gln Val Phe Trp Asp Ser Glu Val Val Glu Ala Tyr Gly Gly Glu Gly
    210                 215                 220

Gly Gly Pro Leu Ala Gly Val Lys Val Lys Asn Leu Val Thr Gly Lys
225                 230                 235                 240

Ile Ser Asp Leu Gln Val Ser Gly Leu Phe Phe Ala Ile Gly His Glu
                245                 250                 255

Pro Ala Thr Lys Phe Leu Gly Gly Gln Leu Glu Leu Asp Ala Asp Gly
            260                 265                 270

Tyr Val Ala Thr Lys Pro Gly Ser Thr His Thr Ser Val Lys Gly Val
        275                 280                 285

Phe Ala Ala Gly Asp Val Gln Asp Lys Lys Tyr Arg Gln Ala Ile Thr
    290                 295                 300

Ala Ala Gly Ser Gly Leu
305                 310
```

<210> SEQ ID NO 28
<211> LENGTH: 32

```
<212> TYPE: DNA
<213> ORGANISM: Artificial Sequence
<220> FEATURE:
<223> OTHER INFORMATION: Description of Artificial Sequence:
      oligonucleotide (oligo P9)

<400> SEQUENCE: 28
gactaagctt acaattatta tatcaaaatg gc                              32

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence:
      oligonucleotide (oligo P10)

<400> SEQUENCE: 29
gcttttccca atacgcaatg c                                          21

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence:
      oligonucleotide (oligo P4)

<400> SEQUENCE: 30
gactagcgct gacagaaact gatgctagga a                               31

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence:
      oligonucleotide (oligo P1)

<400> SEQUENCE: 31
cgtaggatcc accatggctg aagaagaggg tcaggttgtc                      40

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence:
      oligonucleotide (oligo P2)

<400> SEQUENCE: 32
cgtagagctc tcaagaagaa gcagcagcag cagat                           35

<210> SEQ ID NO 33
<211> LENGTH: 29
<212> TYPE: DNA
<213> ORGANISM: Artificial Sequence
<220> FEATURE:
<223> OTHER INFORMATION: Description of Artificial Sequence:
      oligonucleotide (oligo P5)

<400> SEQUENCE: 33
gactagcgct gaagagggtc aggttgtcg                                  29

<210> SEQ ID NO 34
<211> LENGTH: 27
<212> TYPE: DNA
```

```
<213> ORGANISM: Artificial Sequence
<220> FEATURE:
<223> OTHER INFORMATION: Description of Artificial Sequence:
      oligonucleotide (oligo P12)

<400> SEQUENCE: 34
cagtaggctt aaggaggttg caacgag                                          27

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence:
      oligonucleotide (oligo P11)

<400> SEQUENCE: 35
cagtcagctg aagagggtca ggttgtc                                          27

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence:
      oligonucleotide (oligo P27)

<400> SEQUENCE: 36
ctaggagctc tacatggtgt ccaccagcag                                       30

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence:
      oligonucleotide (primer P28)

<400> SEQUENCE: 37
gcacggcttg gtggtgaatc c                                                21

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence:
      oligonucleotide (primer P29)

<400> SEQUENCE: 38
ctcattctgg tccatcaatg tc                                               22

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence:
      oligonucleotide (primer P26)

<400> SEQUENCE: 39
gactgtcgac tcaatcactc ttaccttgct gag                                   33

<210> SEQ ID NO 40
<211> LENGTH: 31
<212> TYPE: DNA
<213> ORGANISM: Artificial Sequence
```

```
-continued

<220> FEATURE:
<223> OTHER INFORMATION: Description of Artificial Sequence:
      oligonucleotide (primer P31)

<400> SEQUENCE: 40
gactggatcc aatggtctcg aaactcacaa c                                  31

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence:
      oligonucleotide (primer thiorodoxubi 1603)

<400> SEQUENCE: 41
gcggtcgttc attcgttcta                                               20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence:
      oligonucleotide (primer thiorodox 2364)

<400> SEQUENCE: 42
acgtgcttca cgatggtgtt                                               20
```